US006977495B2

(12) United States Patent
Donofrio

(10) Patent No.: US 6,977,495 B2
(45) Date of Patent: Dec. 20, 2005

(54) DETECTION CIRCUITRY FOR SURGICAL HANDPIECE SYSTEM

(75) Inventor: William T. Donofrio, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 13 days.

(21) Appl. No.: 10/760,059

(22) Filed: Jan. 16, 2004

(65) Prior Publication Data

US 2004/0147947 A1 Jul. 29, 2004

Related U.S. Application Data

(62) Division of application No. 09/956,359, filed on Sep. 18, 2001, now Pat. No. 6,809,508.
(60) Provisional application No. 60/241,889, filed on Oct. 20, 2000, and provisional application No. 60/242,272, filed on Oct. 20, 2000.

(51) Int. Cl.[7] .................. G01R 15/04; A61B 17/32; A61B 18/18
(52) U.S. Cl. .................. 324/127; 606/169; 606/42
(58) Field of Search .................. 324/127, 118, 324/427, 525, 442; 606/169, 42, 39, 180

(56) References Cited

U.S. PATENT DOCUMENTS

| | | | |
|---|---|---|---|
| 2,917,691 A | 12/1959 | DePrisco et al. ........... 318/118 |
| 4,373,124 A | * 2/1983 | Frame ........................ 200/600 |
| 4,415,959 A | * 11/1983 | Vinciarelli ............... 363/21.04 |
| 4,868,730 A | * 9/1989 | Ward ....................... 363/21.12 |
| 4,924,222 A | * 5/1990 | Antikidis et al. ............. 341/33 |
| 5,001,649 A | 3/1991 | Lo et al. ...................... 364/484 |
| 5,026,387 A | 6/1991 | Thomas ...................... 606/169 |
| 5,112,300 A | 5/1992 | Ureche ........................ 604/22 |
| 5,180,363 A | 1/1993 | Idemoto et al. ............... 202/32 |
| 5,226,904 A | * 7/1993 | Gentelia et al. .............. 606/42 |
| 5,343,140 A | * 8/1994 | Gegner ........................ 323/222 |
| 5,400,267 A | 3/1995 | Denen et al. ............... 364/552 |
| 5,425,704 A | 6/1995 | Sakurai et al. ................ 604/22 |
| 5,449,370 A | 9/1995 | Vaitekunas ................. 606/169 |
| 5,630,420 A | 5/1997 | Vaitekunas ............. 128/662.03 |
| 5,700,969 A | * 12/1997 | Mosley ....................... 102/313 |
| 5,707,369 A | 1/1998 | Vaitekunas et al. ........... 606/31 |
| 5,754,624 A | * 5/1998 | Sullivan et al. .......... 379/27.01 |
| 5,879,364 A | 3/1999 | Bromfield et al. .......... 606/169 |
| 5,897,569 A | * 4/1999 | Kellogg et al. ............. 606/169 |

(Continued)

FOREIGN PATENT DOCUMENTS

JP 07-289577 * 11/1995 ............. A61F/7/00
JP 2000-175926 6/2000

OTHER PUBLICATIONS

European Search Report dated Nov. 20, 2003.

*Primary Examiner*—Ren Yan
*Assistant Examiner*—Wasseem H. Hamdan
(74) *Attorney, Agent, or Firm*—Verne Kreger

(57) ABSTRACT

Various circuit configurations for use in switch assembly used in a surgical hand piece system are provided. The circuit configuration provide a number of functions such as permitting the presence and direction of conductivity to be detected. The circuit configurations also provide a means for detecting and measuring the degree of influence of debris which is located between the conductive members of the handpiece. In addition, the circuit configurations also provide a means for identifying the type of switch end cap which is attached to the handpiece. The handpiece body and the switch mechanism are electrically connected to one another in such a manner that permits the switch end cap to be freely rotated about the handpiece body and reduces the number of conductive members needed to communicate the status of each switch.

13 Claims, 15 Drawing Sheets

U.S. PATENT DOCUMENTS

| | | | |
|---|---|---|---|
| 5,968,007 A | 10/1999 | Simon et al. | 604/22 |
| 6,017,354 A | 1/2000 | Culp et al. | 606/170 |
| 6,019,775 A | 2/2000 | Sakurai | 606/169 |
| 6,028,778 A * | 2/2000 | Amano | 363/40 |
| 6,066,135 A | 5/2000 | Honda | 606/39 |
| 6,090,123 A | 7/2000 | Culp et al. | 606/180 |
| 6,274,963 B1 * | 8/2001 | Estabrook et al. | 310/316.02 |
| 6,339,368 B1 * | 1/2002 | Leith | 340/384.4 |
| 6,580,178 B1 * | 6/2003 | Gale et al. | 290/32 |
| 6,771,518 B2 * | 8/2004 | Orr et al. | 363/16 |

\* cited by examiner

DETECTION CIRCUITRY FOR SURGICAL HANDPIECE SYSTEM

CROSS REFERENCE TO RELATED APPLICATIONS

This application claims the benefit of U.S. provisional patent application Ser. No. 60/241,889, filed Oct. 20, 2000 and U.S. provisional patent application Ser. No. 60/242,272, filed Oct. 20, 2000, and is a division of application Ser. No. 09/956,359, filed on Sep. 18, 2001, now U.S. Pat. No. 6,809,508 B2 Patented on Oct. 26, 2004, all of which are hereby incorporated by reference in their entirety.

BACKGROUND OF THE INVENTION

1. Technical Field

This invention relates to ultrasonic surgical systems and, more particularly, to an improved apparatus for facilitating the performance of surgical procedures such as simultaneous soft tissue dissection and cauterization of large and small blood vessels through the use of a precisely controlled ultrasonically vibrating instrument, such as a blade or scalpel.

2. Background

It is known that electric scalpels and lasers can be used as surgical instruments to perform the dual function of simultaneously effecting the incision and hemostatis of soft tissue by cauterizing tissues and blood vessels. However, such instruments employ very high temperatures to achieve coagulation, causing vaporization and fumes as well as splattering. Additionally, the use of such instruments often results in relatively wide zones of thermal tissue damage.

Cutting and cauterizing of tissue by means of surgical blades vibrated at high speeds by ultrasonic drive mechanisms is also well known. In such systems, an ultrasonic generator is provided which produces an electrical signal of a particular voltage, current and frequency, e.g., 55,500 cycles per second. The generator is connected by a cable to a handpiece, which contains piezoceramic elements forming an ultrasonic transducer. In response to a switch on the handpiece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

The blade is often non-symmetrical in shape and, during the surgical procedure, the physician manipulates the handpiece to cause the blade to contact the tissue to be treated. Because the switch which controls operation of the blade is disposed on the handpiece, the location of the switch may at times prevent the physician from contacting tissue with the desired orientation of the blade because the relative position between the switch and the blade may prevent or render it difficult for the physician to manipulate the blade to the proper position while still being able to activate the switch with his/her fingers.

Thus, there is a need for a handpiece and switch assembly which will permit the physician to freely access tissue and operate thereon without having to worry about the relative position between the switch and the blade.

SUMMARY OF THE INVENTION

Various circuit designs for use in surgical handpiece systems are disclosed herein. The surgical handpiece system includes a switch end cap which is rotatably and preferably detachably connected to the handpiece body with a switch mechanism being provided in the switch end cap. The handpiece body and the switch mechanism are electrically connected to one another in such a manner that permits the switch end cap to be freely rotated about the handpiece body, thereby reducing the number of conductive members needed to communicate the status of each switch.

In one aspect, a sensing circuit is provided within a component of a console which is connected to the handpiece body and provides power thereto. For example, the sensing circuit is designed to detect the presence and direction of conductivity across the conductive members of the handpiece. The switch end cap has a circuit which also permits a reduced number of conductive members to be used to convey signals for monitoring the status of a predetermined number of independent switches, which form a part of the switch end cap. The circuits and the configuration of the conductive members of the handpiece permit the status of two independent switches to be monitored with just two sets of conductive members, rather than the three or more sets of conductive members that would be otherwise required in a more traditional form of circuit monitoring. This reduction in conductive members permits the handpiece construction to be made smaller and more reliable.

In another aspect, the sensing circuit of the handpiece assembly and the circuit of the switch end cap provide a means for detecting and measuring the degree of influence of debris which is located between the conductive members of the handpiece. In addition, the maleffects of such debris is resisted by providing a handpiece using the circuit construction of the present invention.

In yet another aspect, the circuit of the switch end cap in combination with the sensing circuit may be used as a means for identifying the type of switch end cap which is attached to the handpiece body. By varying the circuit used in the switch end cap, the type of switch end cap may be detected by the sensing circuit. Thus, the console, including the sensing circuit, is able to detect what type of switch end cap is attached to the handpiece.

Other features and advantages of the present invention will be apparent from the following detailed description when read in conjunction with the accompanying drawings.

BRIEF DESCRIPTION OF THE DRAWINGS

The foregoing and other features of the present embodiments will be more readily apparent from the following detailed description and drawings of illustrative embodiments in which.

DESCRIPTION OF ILLUSTRATIVE EXEMPLARY EMBODIMENTS

Figure 1:
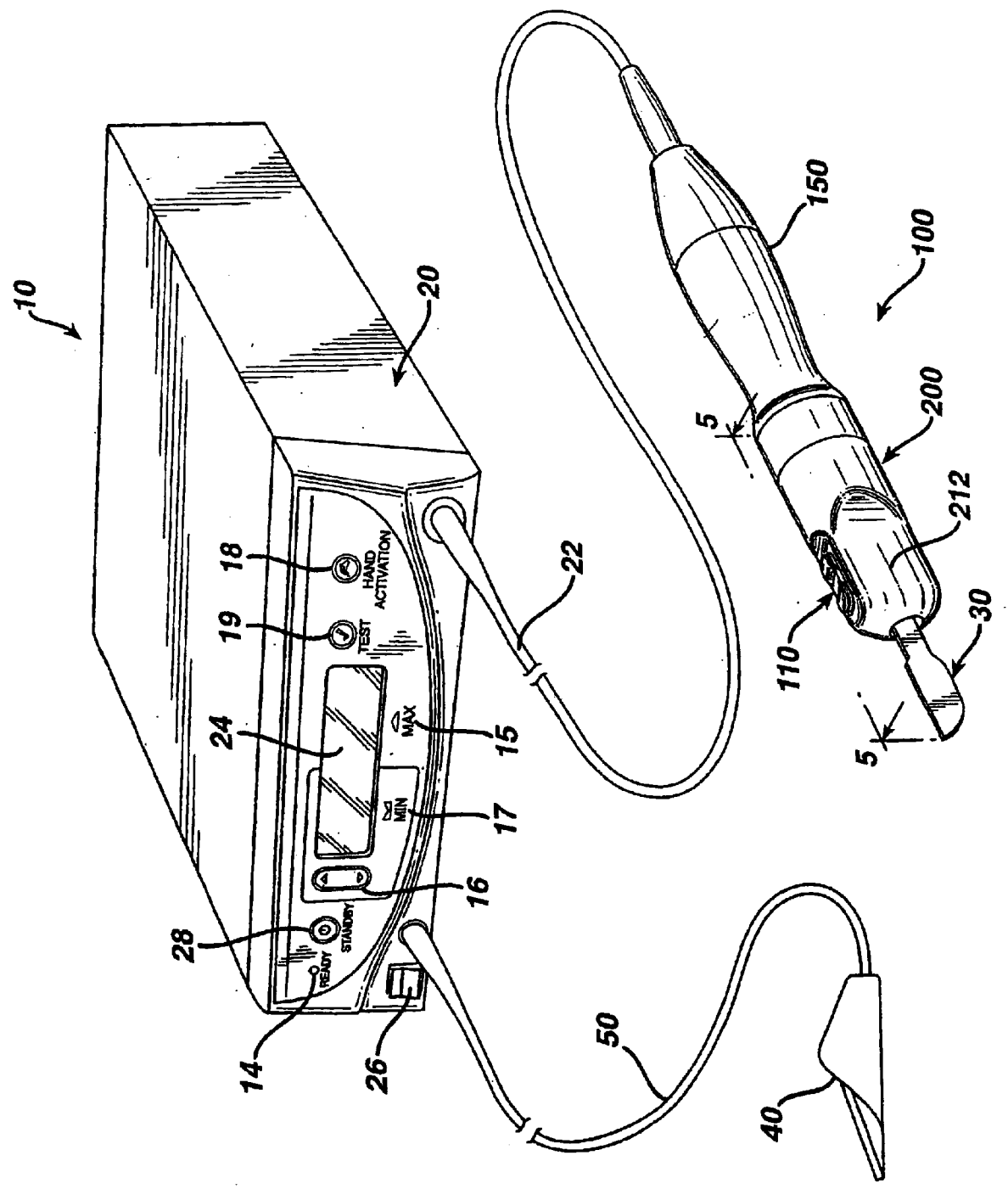
FIG. 1 is an illustration of a console for an ultrasonic surgical cutting and hemostatis system, as well as a handpiece and foot switch in accordance with an exemplary embodiment.

Referring first to FIG. 1 in which an ultrasonic surgical cutting and hemostatis system according to one embodiment is illustrated and generally indicated at 10. The system 10 includes a console or housing 20 for containing an ultrasonic generator (not shown) and a control system located within the console 20 which forms a part of the system 10. A first cable 22 connects the console 20 to a handpiece 100 and serves to provide an electrical connection therebetween. The first cable 22 includes a first set of wires (not shown) which permit electrical energy, i.e., drive current, to be sent from the console 20 to the handpiece 100 where it imparts ultrasonic longitudinal movement to a surgical instrument 30. According to an exemplary embodiment, the surgical instrument 30 is preferably a sharp scalpel blade or shear. This instrument 30 can be used for simultaneous dissection and cauterization of tissue.

The supply of ultrasonic current to the handpiece 100 is controlled by a switch mechanism 110 disposed within the handpiece 100. As will be described in greater detail hereinafter, the switch mechanism 110 is connected to the console 20, more specifically the generator thereof, by one or more wires (not shown) of the first cable 22. The generator may also be optionally and further controlled by a foot switch 40 which is connected to the console 20 by a second cable 50. Thus, in use, a surgeon may apply an ultrasonic electrical signal to the handpiece 100, causing the instrument 30 to vibrate longitudinally at an ultrasonic frequency, by operating the switch mechanism 110 on the handpiece 100 or the foot switch 40. The switch mechanism 110 is activated by the hand of the surgeon and the foot switch 40 is activated by the surgeon's foot.

The generator console 10 includes a liquid crystal display device 24, which can be used for indicating the selected cutting power level in various means such as percentage of maximum cutting power or numerical power levels associated with cutting power. The liquid crystal display device 20 can also be utilized to display other parameters of the system. Power switch 26 is used to turn on the unit. While it is warming up, the "standby" light 28 is illuminated. When it is ready for operation, the "ready" indicator 14 is illuminated and the standby light goes out. If the unit is supplying maximum power, the MAX indicator is illuminated. If a lesser power is selected, the MIN indicator is illuminated. The level of power when MIN is active is set by button 16.

If a diagnostic test is to be performed, it is initiated by the "test" button 19. For safety reasons, e.g., to make sure a test is not started while the blade is touching the surgeon or other personnel, the button 19 may be depressed in combination with switch mechanism 110 or foot switch 40. Also, if the switch mechanism 110 is to be operative instead of foot switch 40, "hand activation" button 18 on the front panel must be selected or enabled using button 18.

When power is applied to the ultrasonic hand piece 100 by operation of either switch mechanism 110 or switch 40, the assembly will cause the surgical scalpel or blade 30 to vibrate longitudinally at approximately 55.5 kHz, and the amount of longitudinal movement will vary proportionately with the amount of driving power (current) applied, as adjustably selected by the user. When relatively high cutting power is applied, the blade 30 is designed to move longitudinally in the range of about 40 to 100 microns at the ultrasonic vibrational rate. Such ultrasonic vibration of the blade 30 will generate heat as the blade contacts tissue, i.e., the acceleration of the blade through the tissue converts the mechanical energy of the moving blade 30 to thermal energy in a very narrow and localized area. This localized heat creates a narrow zone of coagulation, which will reduce or eliminate bleeding in small vessels, such as those less than one millimeter in diameter. The cutting efficiency of the blade, as well as the degree of hemostasis, will vary with the level of driving power applied, the cutting rate of the surgeon, the nature of the tissue type and the vascularity of the tissue.

Referring now to FIGS. 2–7, in which the handpiece 100 is illustrated in greater detail, the ultrasonic handpiece 100 houses a piezoelectric transducer, generally indicated at 120, for converting electrical energy to mechanical energy that results in longitudinal vibrational motion of the ends of the transducer. The transducer 120 is preferably in the form of a stack of ceramic piezoelectric elements with a motion null point between the end of the stack. A horn 130 is coupled to the transducer 120 on one side. Instrument 30 is fixed to a portion of the horn 130. As a result, the instrument 30 will vibrate in the longitudinal direction at the ultrasonic frequency rate of the transducer 120. The ends of the transducer 120 achieve maximum motion when the transducer 120 is driven with a current of 380 mA RMS at the transducer resonant frequency. This is merely a general overview of the operation of the handpiece 100 and one of skill in the art will appreciate how the specific components operate to accomplish the ultrasonic surgical action.

The parts of the handpiece 100 are designed such that the combination will oscillate at the same resonant frequency. In particular, the elements contained therein are tuned such that the resulting length of each element is one-half wavelength. Longitudinal back and forth motion is amplified as the diameter closer to the instrument 30 of the acoustical mounting horn 130 decreases. Thus, the horn 130, as well as the instrument 30, are shaped and diminished so as to amplify blade motion and provide harmonic vibration in resonance with the rest of the acoustic system, which produces the maximum back and forth motion of the end of the acoustical mounting horn 130 close to the instrument 30.

The handpiece 100 includes a body 150 which contains internal operating components, such as but not limited to the transducer 120 and the horn 130. The body 150 is designed to mate with a switch end cap 200 (FIG. 2) which is rotatably coupled to the body 150, as will be described in greater detail hereinafter. Preferably, the switch end cap 200 is detachably connected to the body 150. The body 150 has a distal end 152 and an opposing proximal end 154 which attaches to one end of the cable 22. The body 150 may have any number of shapes and is designed so that a user may easily grip and comfortably hold the handpiece 100 in one's hand. Preferably, the body 150 is generally annular in shape and in the exemplary embodiment, the handpiece 100 has a design with multiple tapered sections permitting the user to grasp and rest a thumb and one or more fingers around the handpiece 100. In the illustrated embodiment, the body 150 is formed of a metal material; however, one will appreciate that the body 150 may be formed of a number of materials, including but not limited to plastic materials.

At the proximal end 154, an electrical adapter 156 is provided and is electrically connected to the cable 22 by means of one or more wires (not shown). The electrical adapter 156 is also electrically connected to other internal components of the handpiece 100 so that power may be selectively provided to the handpiece 100 using the switch mechanism 110, as will be described in greater detail hereinafter. The proximal end 154 is generally closed ended with the cable 22 being routed therethrough, while the distal end 152 is at least partially open ended. The horn 130 extends in the direction of the distal end 152 such that a distal tip 132 of the horn 130 extends beyond the distal end 152 of the handpiece 100. The distal tip 132 has a stud 456 or the like extending outwardly therefrom. Preferably, the stud 456 comprises a threaded stud and is designed to threadingly mate with the instrument 30 to secure the instrument 30 to the handpiece 100. The instrument 30 has a blade portion 32 (FIG. 5) with an insulative sheath 34 disposed about the blade portion 32. The blade portion 32 also has an exposed blade tip 36 which extends beyond the insulative sheath 34 so as to be available for contacting and cutting tissue and the like. The insulative sheath 34 is formed of any number of suitable insulative materials, and in one exemplary embodiment is formed of a plastic material.

Figure 2:
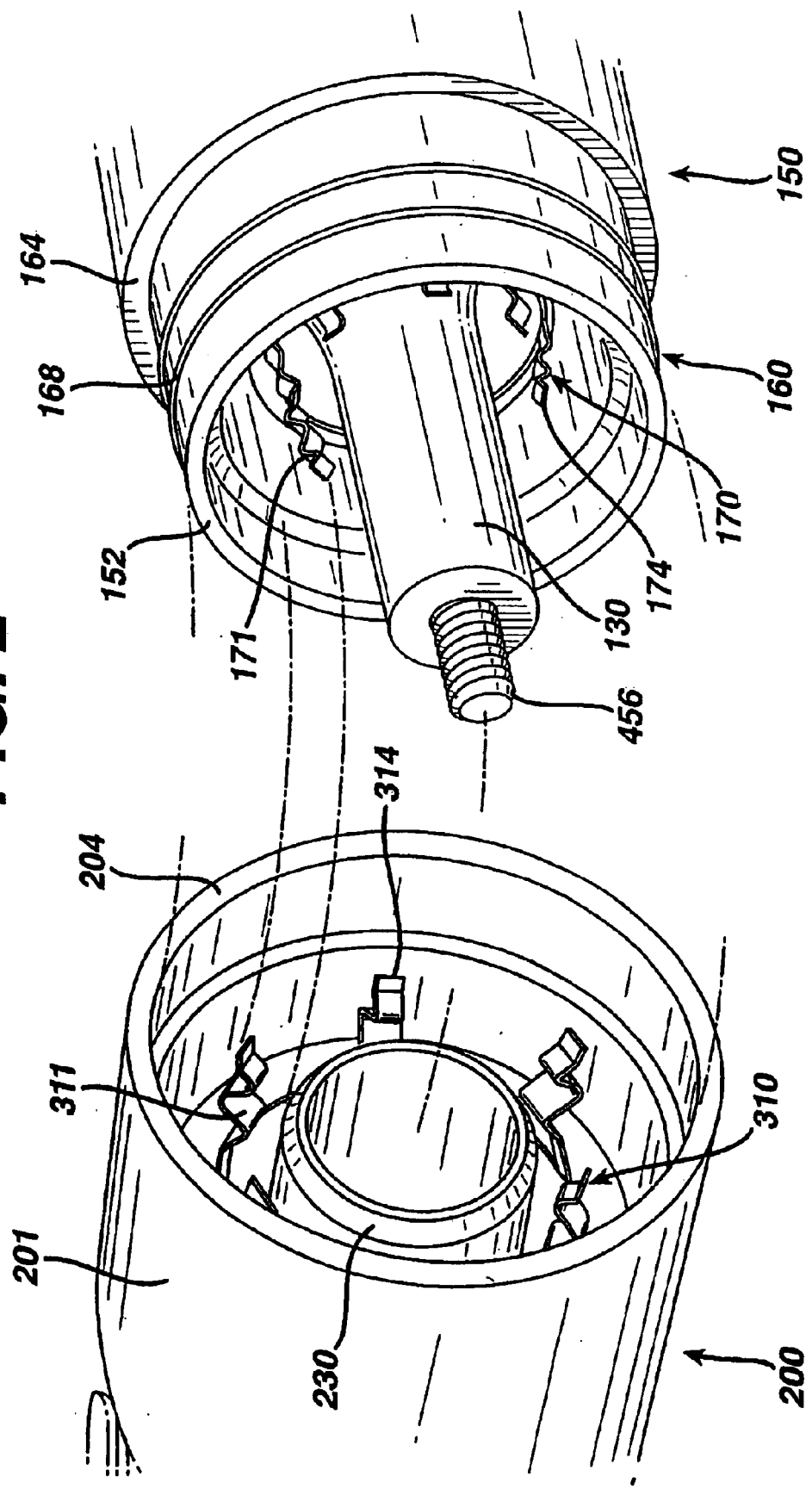
FIG. 2 is a fragmentary perspective view of one exemplary handpiece and switch end cap.
Figure 3:
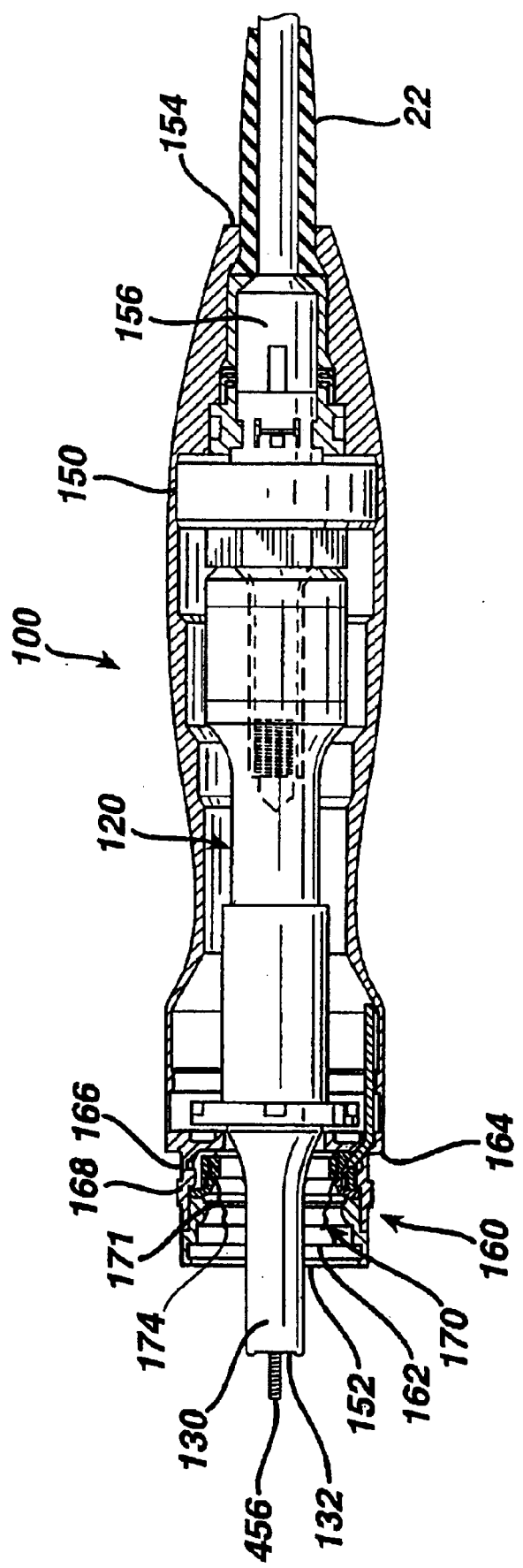
FIG. 3 is a longitudinal cross-sectional view of the handpiece.

At the distal end 152, the body 150 has a reduced diameter so as to form a flange member 160 (FIG. 3). The flange member 160 defines a cavity 162 through which the horn 130 extends. In the illustrated embodiment, the flange member 160 is annular in shape and extends to a location just before the distal tip 132 of the horn 130 so that a portion of the horn 130, including the distal tip 132, extends beyond the end of the flange member 160. A shoulder 164 is formed at the location where the flange member 160 extends from the remaining portion of the body 150. An outer surface 166 of the flange member 160 may include one or more ridges, generally indicated at 168, which extend annularly around the outer surface 166. In the illustrated embodiment shown in FIG. 2, there are two ridges 168 in the form of threads spaced apart from one another and, because of the annular shape of the outer surface 166, the ridges 168 comprise annular threads. It will be appreciated that the outer surface 166 is constructed so that it complementarily mates with the switch end cap 200.

Figure 7:
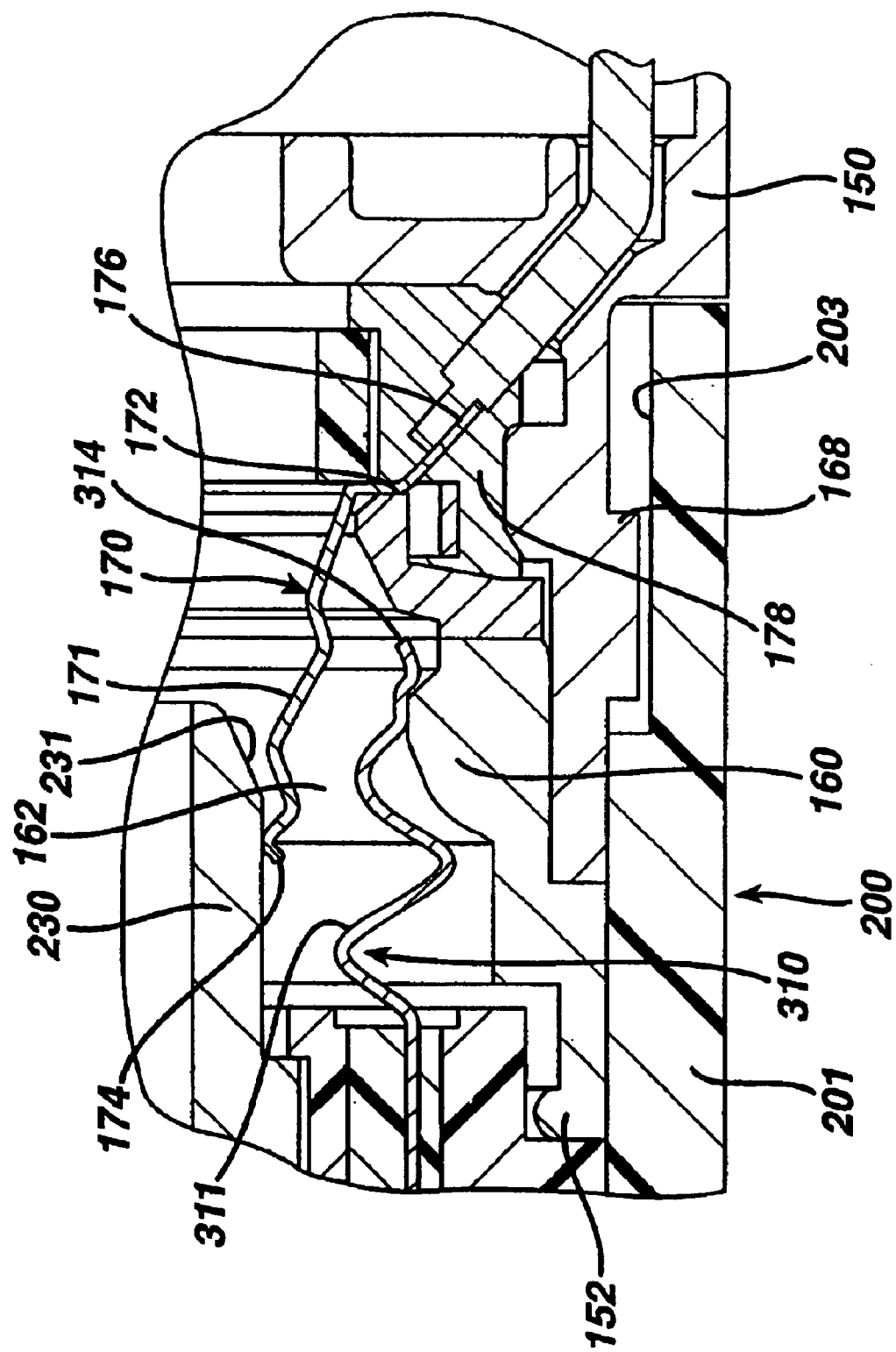
FIG. 7 is a fragmentary enlarged cross-sectional view of the electrical connection between the switch end cap and the handpiece body and taken along the line 7—7 of FIG. 4.

As best shown in FIGS. 2 and 7, the body 150 also includes a first conductive finger element 170 which is disposed about the horn 130 within the cavity 162. In the exemplary embodiment, the first conductive finger element 170 is an annular ring-like member formed of a plurality of fingers 171 radially disposed about the horn 130. Each finger 171 of the conductive finger element 170 has a serially-connected first section 172 and a second section 174, which comprises a free end of the finger 171. The free second section 174 electrically engages another conductive member when the handpiece 100 is assembled, as will be described in greater detail hereinafter. The second section 174 is preferably bent in several locations so that it assumes a generally zig-zag shape and is resilient so that the fingers 171 may be bent outwardly under an applied force. It will be appreciated that instead of having a plurality of fingers 171, only a single finger 171 may be provided.

At the proximal end of the first section 172, each finger 171 connects to a first conductive base ring, generally indicated at 176, which provides a conductive path between all of the fingers 171. The first conductive base ring 176 is also used to properly locate and position the first conductive finger element 170 within the body 150 and more specifically, within the cavity 162. The first conductive base ring 176 is anchored within the body 150 and is electrically isolated from the conductive body 150 by using one or more spacers 178 which are disposed between the body 150 within the cavity 162 and the ring 176. Because of the annular shape of the body 150 and the horn 130, the one or more spacers 178, generally in the form of insulative ring structures, are disposed between the fingers 171 and the conductive body 150. Typically, the one or more spacers 178 are formed of any number of suitable plastic materials or elastomeric materials. The first conductive finger element 170 is also spaced a sufficient distance from the horn 130, which is also formed of a conductive material, e.g., metal, so that the fingers 171 or other part of the element 170 do not make contact with the horn 130 during assembly of the handpiece 100. By disposing the one or more spacers 178 between the fingers 171 and the body 150, the spacer 178 serves to slightly urge the fingers 171 inwardly away from a conductive inner surface 151 of the body 150.

As previously mentioned with respect to FIG. 3, the cable 22 serves to provide power to the handpiece and accordingly, the first conductive finger element 170 is electrically connected to the electrical adapter 156 by means of one or more electrical wires (not shown) which extend along a length of the body 150 from the electrical adapter 156 to the first conductive finger element 170. It will also be appreciated and will be described in greater detail hereinafter, that the body 150 itself serves as an electrical pathway or wire because the body 150 is electrically connected to the cable 22.

Figure 4:
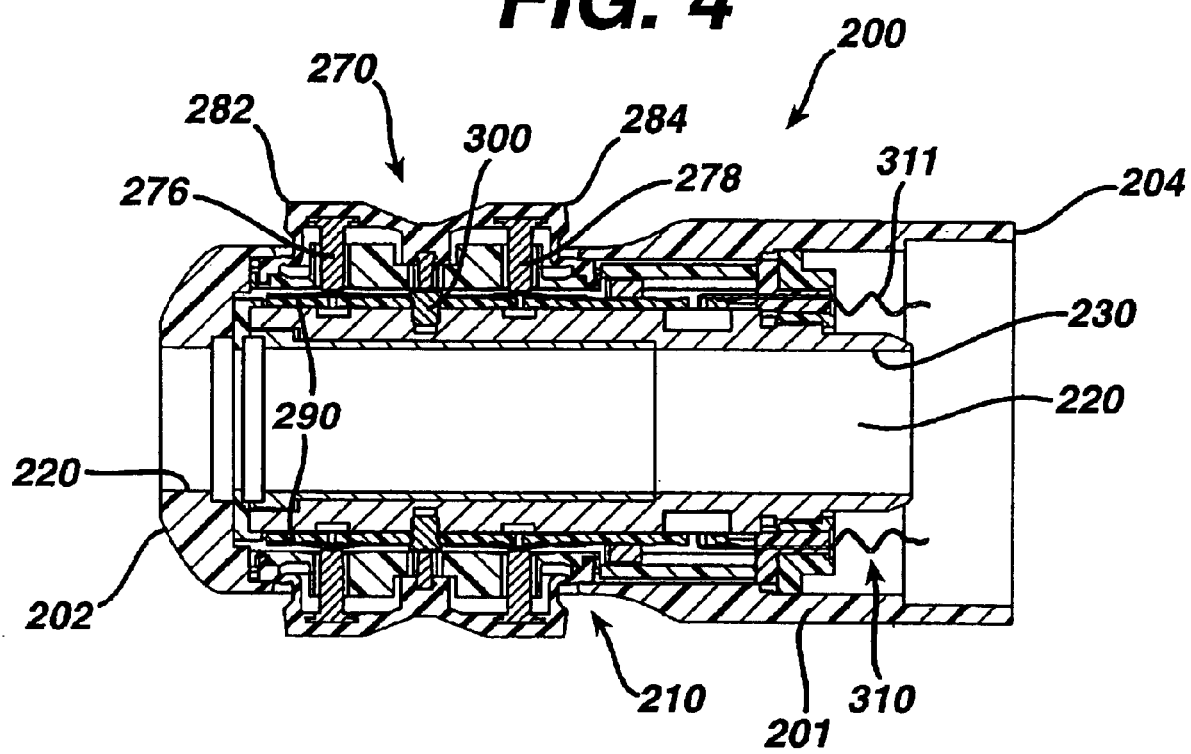
FIG. 4 is a longitudinal cross-sectional view of the switch end cap.

As best shown in FIGS. 4–7, the switch end cap 200 mates with the body 150 so that the switch end cap 200 may freely rotate about the handpiece body 150 during operation of the handpiece 100. The switch end cap 200 is formed of an outer shell 201 having a distal end 202 and an opposing proximal end 204 with the proximal end 204 of the switch end cap 200 receiving and mating with the distal end 152 of the body 150 (FIG. 4). The shell 201 has an outer surface 206 (FIG. 7) which is contoured to be gripped and held by a user during operation of the handpiece 100. The proximal end 204 of the shell 201 is generally annular in nature and the exemplary shell 201 slightly tapers inwardly to form a switch section 210 close to the distal end 202. This slight taper forms finger shaped recessed portions which permit the fingers of a user to easily grip and hold the shell 201 as during coupling of the switch end cap 200 to the body 150 or during rotational movement of the switch end cap 200 relative to the body 150.

Figure 6:
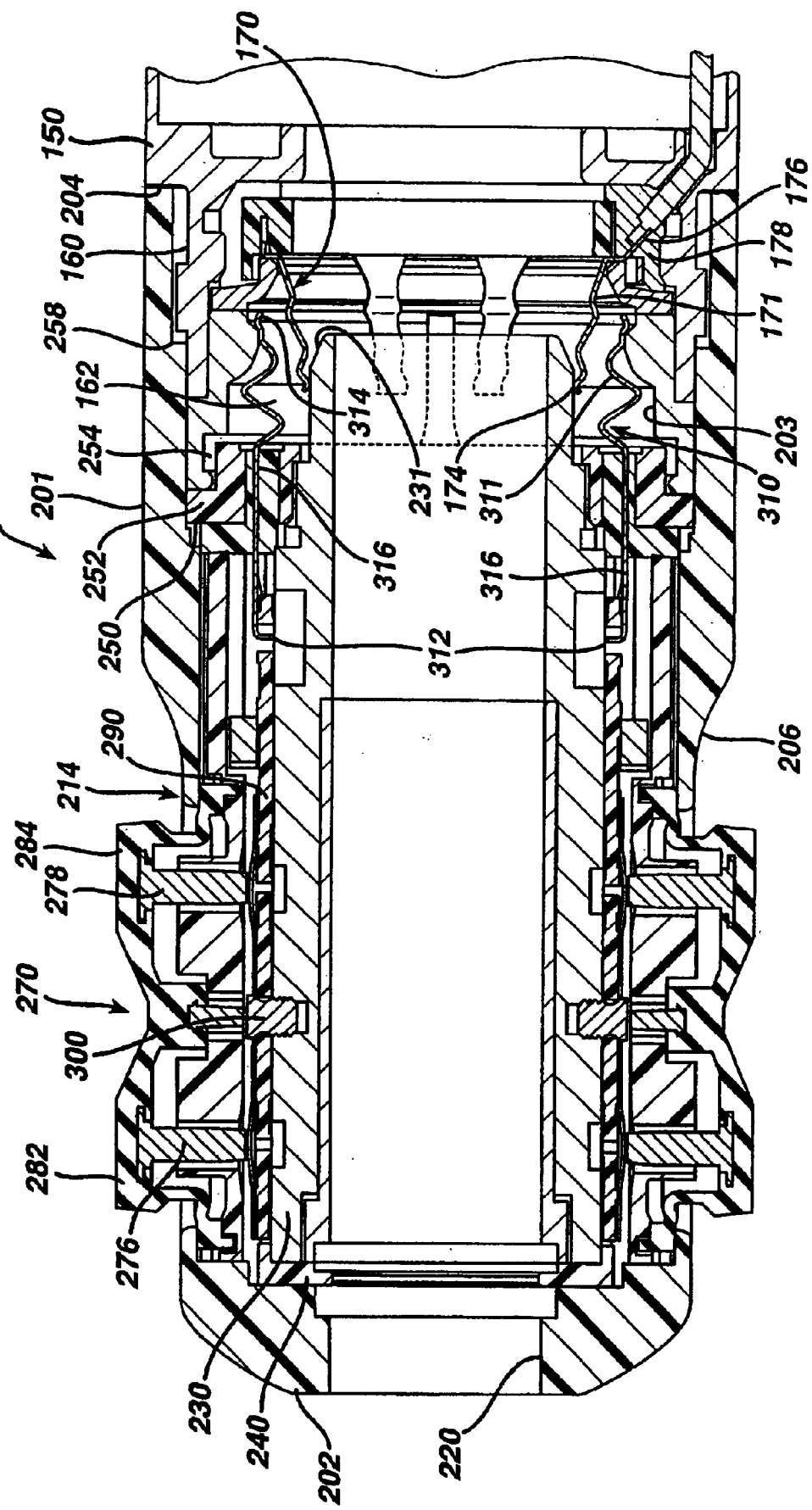
FIG. 6 is an enlarged cross-sectional view showing the switch end cap with a portion of the outer surface broken away.

The switch section 210 is actually formed of a pair of opposing contoured finger sections, generally indicated at 212 (FIG. 1), and a pair of opposing recessed button sections, generally indicated at 214 (FIG. 6). Preferably each finger section 212 is formed about 180° apart from the other finger section 212 and one recessed button section 214 is formed about 180° apart from the other button section 214. The holding and rotational manipulation of the shell 201 is done by placing a thumb on one finger section 212 and a finger, i.e., the middle finger, in the other of the finger sections 212. This permits the index finger to rest upon one of the button sections 214. Each button section 214 is slightly tapered relative to the proximal end 204, while the taper to form the finger sections 212 is more pronounced to accommodate resting locations for the thumb and one or more fingers.

The outer shell 201 is at least partially open at both the distal end 202 and the proximal end 204 with a bore 220 extending therethrough (FIG. 4). The bore 220 is sized to receive a first conductive member 230 which is securely located within the switch end cap 200 by disposing the first conductive member 230 within the bore 220. In the exemplary embodiment, the first conductive member 230 comprises a cylindrical member formed of a suitable conductive material, such as a metal. The first conductive member 230 extends along a length of the outer shell 201 from a point near the distal end 202 to a point near the proximal end 204. Preferably, the diameter of the opening at the distal end 202 is about the same size as the diameter of the conductive member 230 and is axially aligned therewith so as to permit access to the inside of the conductive member 230 so that the instrument 30 may inserted therein and the inside of the conductive member 230 may be cleaned, etc.

Figure 5:
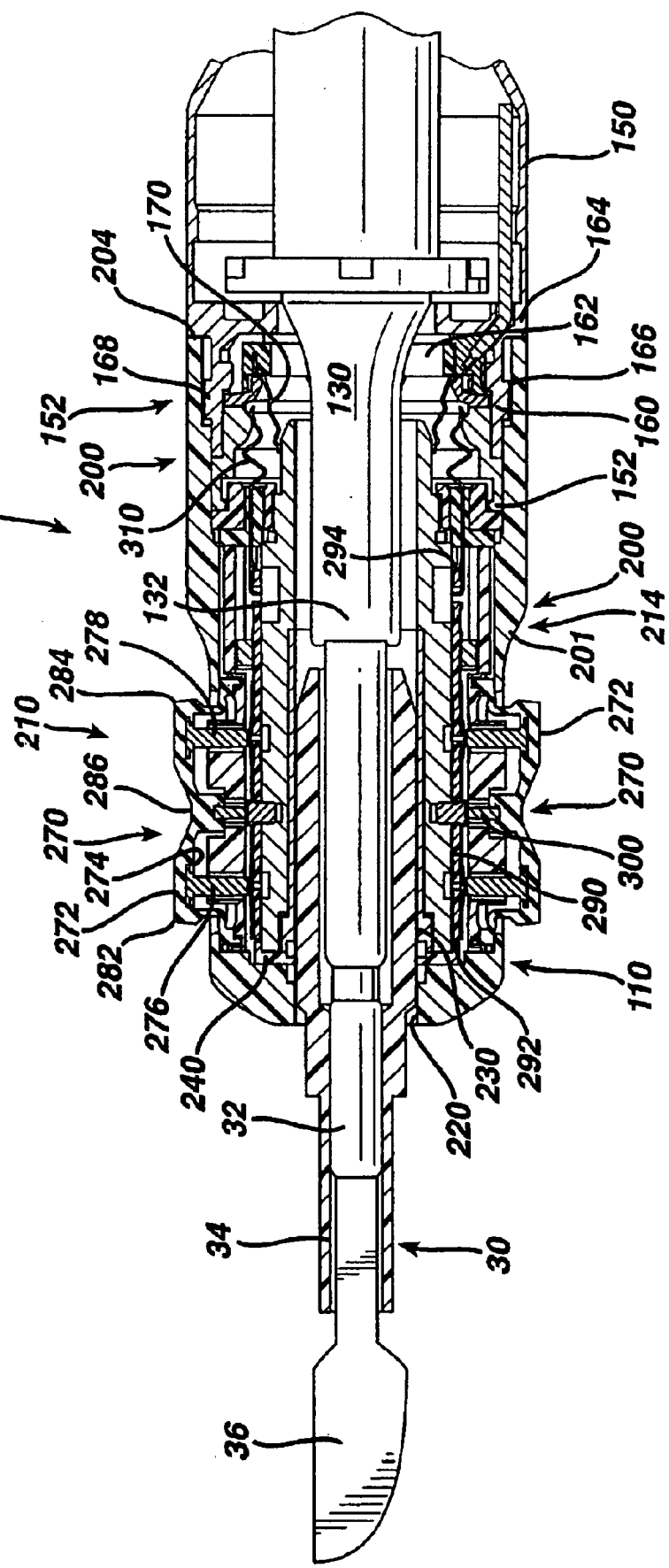
FIG. 5 is a cross-sectional view of the handpiece and switch end cap taken along the section line 5—5 of FIG. 1.

As best shown in FIGS. 5 and 6, at the distal end 202, a seal member 240 is disposed at the end of the conductive member 230. More specifically, the seal member 240 is retained in a groove formed in the shell 201 adjacent to the conductive member 230. The seal member 240 is preferably formed of an elastic material, preferably an elastomeric material, and more preferably is formed of silicon. As will be described in greater detail hereinafter, the seal member 240 is designed to prevent unwanted foreign matter from entering the inside of the conductive member 230. When the switch end cap 200 mates with the handpiece body 150, the instrument 30 extends through the conductive member 230 and exits through the opening formed at the distal end 202 of the switch end cap 200. Accordingly, the instrument 30 extends through the seal member 240. Due to the elastic nature of the seal member 240, the seal member 240 engages the sheath 34 of the instrument 30 to produce a seal therebetween. This seal prevents the unwanted foreign matter from entering through the opening formed at the distal end 202 of the shell 201 because any matter that might enter, during a surgical operation, is restricted by the seal member 240.

As best shown in FIG. 6, near the proximal end 204, the switch end cap 200 has an annular platform 250 formed thereat which is preferably concentric to the conductive member 230. The annular platform 250 has an opening formed at the center thereof because the bore 220 is formed through the annular platform 250 and more specifically, one end of the bore 220 begins at the annular platform 250. The annular platform 250 extends radially inwardly toward the proximal end 204 and away from another annular surface 252 which extends between the inner surface 203 of the shell 201. Because the annular platform 250 preferably has a diameter less than the diameter defined by the inner surface 203 of the outer shell 201, a gap 254 is formed between the annular platform 250 and an inner surface 203 of the shell 201. The annular platform 250 may thus be thought of as a spacer member. The conductive member 230 has a length such that a section of the conductive member 230 extends beyond the annular platform 250 into a cavity formed between the inner surface 203 of the shell 201 at the proximal end 204. The inner diameter of the shell 201 near the proximal end 204 may vary slightly due to one or more lip portions 258 being formed on the inner surface 203 of the shell 201. These one or more lip portions 258 serve to provide engaging surfaces for the handpiece 100 when the handpiece body 150 is coupled to the switch end cap 200.

As best shown in FIGS. 5 and 6, the switch end cap 200 also includes a pair of switch button members 270 which are detachably secured within the button sections 214 formed in the outer shell 201. Each switch button member 270 has an upper surface 272 and includes a flange 274 seating against a retainer 275 formed as part of the outer shell 201. The flange 274 seals with the retainer 275 so to prevent any foreign material and the like from entering the electronic switch components of the switch mechanism 110. The retainer 275 is preferably attached to the outer shell 201 by conventional techniques, including a snap-fit arrangement. First and second posts 276, 278, respectively, extend outwardly from the switch button member 270. The first and second posts 276, 278 are spaced apart from one another with a center traverse wall 280 being formed therebetween. The upper surface 272 includes a first raised section 282 and a second raised section 284 spaced therefrom with a center recessed section 286 being formed therebetween. The upper surface 272 is thus slightly beveled as the switch button member 270 transitions from the center recessed section 286 to the first and second raised sections 282, 284. In the illustrated embodiment, the first post 276 is disposed generally below the first raised section 282 and the second post 278 is disposed generally below the second raised section 284 so that when a user presses downwardly upon the first raised section 282, the first post 276 is also directed downward. Similarly, when the user presses downwardly upon the second raised section 284, the second post 278 is directed downward.

The switch button members 270 are each designed to act as a depressable switch button for selectively causing activation of the handpiece 100 as will be described in greater detail hereinafter. The switch button members 270 are formed of suitable materials, such as plastic materials, and preferably the switch button members 270 are formed of a resilient plastic material. In one exemplary embodiment, the switch button members 270 are formed of silicon which permits the members to be sufficiently resilient enough so that they may be fitted and secured within the button sections 214 and also provide an engagement surface for a finger or thumb during operation of the handpiece 100. In one aspect of the present invention, the contour of the switch button member 270 permits a fingertip to easily rest between the first and second raised sections 282, 284. In other words, the finger tip seats and rests within the center recessed section 286 without actuating the switch mechanism 110. Because the switch button members 270 are disposed within the button sections 214, the switch button members 270 are spaced about 180° from one another. The recessed section 286 advantageously provides a location for the user to rest a finger during operation of the switch button member 270 without inadvertently activating the switch button member 270. This results because the recessed section 286 is above the pivot point of the switch button member 270.

The switch end cap 200 also includes a pair of printed circuit boards (PCBS) 290 which form a part of the electronic switch mechanism 110. The PCBs 290 are disposed within the outer shell 201 such that the PCBs 290 are disposed between the conductive member 230 and the switch button members 270. The PCBs 290 extend longitudinally relative to an axis extending through the bore 220 formed in the switch end cap 200. A distal end 292 of each PCB 290 is located near the distal end 202 of the switch end cap 200 and proximate to the seal member 240. The PCB 290 has a proximal end 294 opposite the distal end 292. It will be understood that instead of using PCBs 290, other suitable electronic components may be used, such as a flexible circuit component known as a "flexprint".

A pair of fasteners 300 serve to electrically connect the PCBs 290 to the conductive member 230. More specifically, one side of a switch circuit according to the present invention is defined by the conductive member 230 since the PCB 290 is electrically connected thereto. The pair of fasteners 300 extend through openings (not shown) formed in the PCBs 290 to provide the desired electrical connection between the PCBs 290 and the conductive member 230.

As shown in FIG. 5, the pair of fasteners 300 are positioned beneath the center traverse wall 280. Each button section 214 formed in the outer shell 201 contains openings formed therein and spaced apart from one another for receiving the first and second posts 276, 278 of the switch button member 270. The exemplary switch mechanism 110 is known as a rocker type switch mechanism and, according to one embodiment, two switch button members 270 form, in part, the switch mechanism 110. Each switch button member 270 has two switch settings. For example, the first raised section 282 and the first post 276 are associated with a first switch setting and the second raised section 284 and the second post 278 are associated with a second switch setting. Preferably, the first switch setting of one switch button member 270 is the same as the first switch setting of the other switch button member 270 disposed about 180° therefrom. In one exemplary embodiment, the first switch setting is a maximum power setting and the second switch setting is a minimum power setting (or a lesser power setting than the maximum setting). It will be understood that the opposite may equally be true, in that the first switch setting may be designed for causing the transmission of minimum power to the handpiece 100 and the second switch setting will then cause the transmission of maximum power to the handpiece 100.

The PCBs 290 are thus also designed to provide a circuit having two different switch settings. It will also be appreciated that any number of PCBs 290 may be used in the practice of the present invention so long as the PCBs 290 contain circuits which provide signals to the generator or the like causing the delivery of at least two different levels of power to the handpiece 100 depending upon which portion of the switch button member 270 is contacted by the user. One preferred type of PCB 290 is a dome switch type PCB 290 in which a first dome (not shown) is formed as part of the PCB 290 for generating a first signal (e.g., a maximum power signal) when the first dome is collapsed under an applied force. The dome switch type PCB 290 also includes a second dome (not shown) formed as part of the PCB 290 for generating a second signal (e.g., a minimum power signal) when the second dome is collapsed under an applied force. It will be understood that the switch mechanism 110 of the present invention is not limited to generating signals for controlling the delivery of power to the handpiece 10. The switch mechanism 110 may also be used to generate signals which control other functions of the handpiece 10. For example, the control signals may be used to selectively control console functions, including but not limited to, a stand-by function, a diagnostic function, and turning the console 20 on and off.

The first dome is disposed underneath the first post 276 so that when the user depresses the first raised section 282, the switch button member 270 pivots about the fastener 300 and the first post 276 is directed downwardly through the respective opening formed in the button section 214 until contact is made between the first post 276 and the PCB 290. More specifically, the first post 276 contacts the first dome of the PCB 290 and causes the first dome to collapse. When the first dome collapses, electrical current flows in a first direction through the PCB 290 and generally through the switch mechanism 110. When the user depresses the second raised section 284, the second post 278 contacts and collapses the second dome and causes electrical current to flow in an opposite second direction through the PCB 290 and generally through the switch mechanism 110. It will also be understood that the present invention is not limited to the use of domes but rather any mechanism which serves to close a normally open switch may be used in the practice of the present invention. The collapsing motion of a dome is merely one exemplary way of closing a normally open switch.

As best shown in FIGS. 6 and 7, the switch end cap 200 also includes a second conductive finger element 310 which is disposed about the proximal end of the conductive member 230. In the exemplary embodiment, the second conductive finger element 310 is an annular ring-like member formed of a plurality of fingers 311 radially disposed about the conductive member 230. Each finger 311 of the conductive finger element 310 has a first section 312 which is electrically connected to one of the PCBs 290 and a serially-connected second section 314 which comprises a free end of the finger 311. The free second section 314 makes electrical contact to another conductive member when the handpiece 100 is assembled as will be described in greater detail hereinafter. The second section 314 is preferably bent in several locations so that it assumes a generally zig-zag shape. The first and second conductive finger elements 170, 310 may be formed of any number of suitable conductive materials.

Between the first and second sections 312, 314, each finger 311 connects to a conductive base ring, generally indicated at 316, which provides a conductive path between all of the fingers 311 (FIG. 7). The conductive base ring 316 also is used to properly locate and position the conductive finger element 310 within the switch end cap 200. The annular platform 250 preferably includes a plurality of radially spaced tabs (not shown) which serve to retain the conductive finger element 310 by inserting the conductive base ring 316 underneath the tabs such that the second section 314 of the finger 311 is located between and extends outwardly from adjacent tabs. By anchoring the conductive finger element 310 within the annular platform 250, the second sections 314 of the plurality of fingers 311 may be manipulated and moved in directions generally towards or away from the conductive member 230. The number of fingers 311 may vary depending upon the precise application and in one exemplary embodiment, the conductive finger element 310 includes six (6) fingers 311. The fingers 311 also provide a mechanism for releasably retaining the switch end cap 200 to the flange 160. When the switch end cap 200 is mated with the handpiece body 150, the fingers 311 are flexed inward by engagement with the inner surface of the body 150. This inward flexing of the fingers 311 causes the fingers 311 to apply an outwardly directed biasing force against the flange 160 causing retention between the switch end cap 200 and the body 150. Because the conductive finger element 310 provides, in part, an electrical path for the handpiece 100, it is important that the conductive finger element 310 not touch the conductive member 230. It will be appreciated that the switch end cap 200 preferably includes a number of other spacer members which serve to further isolate the conductive members of the switch end cap 200, namely the element 310 and member 230.

All of the conductor members used in the surgical device 10 (FIG. 1) of the various embodiments are formed of any number of suitable conductive materials. In one exemplary embodiment, the conductive members are formed of stainless steel, gold plated copper, beryllium copper, titanium nitride, or conductive plastics which serve to reduce the tendency of the members to corrode from harsh cleaning solutions or autoclaving.

The assembly and operation of the handpiece 100 will now be described with reference to FIGS. 1–7. The switch end cap 200 is removably attached to the handpiece body 150 by aligning the stud 456 and the horn 130 with the inside of the conductive member 230. After the stud 456 and the horn 130 are aligned with the bore formed in the conductive member 230, the switch end cap 200 is brought into engagement with flange member 160 causing the stud 456 and a portion of the horn 130 to be disposed inside of the conductive member 230 when the switch end cap 200 is properly fitted about the body 150. However, the stud 456 and the horn 130 do not make contact with the conductive member 230 when switch end cap 200 is attached to the body 150. The proximal end 204 of the switch end cap 200 seats proximate to or against the shoulder 164. Stop 391 formed in the switch end cap 200 engages the distal end 152 of the body 150, thereby providing a stop which restricts further movement of the switch end cap 200.

Because the stud 456 and a portion of the horn 130 are disposed inside of the conductive member 230 at a proximal end thereof, the instrument 30 is secured within the switch end cap 200 by securing the instrument 30 to the stud 456. More specifically, the instrument 30 preferably has a threaded bore formed therein at an end opposite the blade tip 36 (FIG. 3). The instrument 30 preferably attaches to the stud 456 by threadingly engaging the threaded bore with the threaded stud 456 resulting in the instrument 30 being secured to the stud 456. The instrument 30 is easily removed for cleaning or replacement thereof by simply twisting the instrument 30 in one direction until the instrument 30 disengages the stud 456. When the instrument 30 is secured to the stud 456, the insulative sheath 34 of the instrument 30 contacts and forms a seal with the seal member 240 so that unwanted foreign matter is prevented from traveling through the opening formed in the distal end 202. Because of the resilient nature of the seal member 240, the seal member 240 conforms to the blade shape and the resilient nature of the insulative sheath 34 further provides an effective seal.

In accordance with another aspect of the present invention, the first and second conductive finger elements 170, 310 provide an electrical pathway between the switch mechanism 110 of the switch end cap 200 and the cable 22, which provides the means for delivering power to the handpiece 100. As best shown in FIG. 7, when the switch end cap 200 is attached to the body 150 and the fingers 171 of the first conductive finger element 170 contact and are biased against an outer surface 231 of the first conductive member 230 of the switch end cap 200. This results because the first conductive member 230 is disposed between the fingers 171 and the horn 130 as the switch end cap 200 is attached. Because of the conductive nature of both the first conductive member 230 and the fingers 171, an electrical pathway is formed between the PCBs 290 and the cable 22. This electrical connection also serves to complete one side of the circuit of the switch mechanism 110 when one of the switch button members 270 is depressed to cause one of the domes to collapse, thereby permitting current to flow through the PCBs 290. Once the user releases either of the first and second raised sections 282, 284 (which the user had previously depressed), the dome expands and the electrical pathway is interrupted, thereby interrupting the flow of current through the switch mechanism 110. This stops the delivery of power to the handpiece 100. It will also be appreciated that the switch mechanism 110 may include only a single button member 270.

While, the switch mechanism 110 has been generally discussed as being a normally open switch assembly in which a mechanism (such as one or more domes) is activated to cause the closing of the switch, one of skill in the art will appreciate that the switch mechanism 110 may be a normally closed switch assembly. In this embodiment, depressing one of the sections 282, 284 will cause one of the switches to open and not close as in the other embodiment. Because the dual switch mechanism 110 has current flowing in first and second opposing directions, the opening of one switch will leave current flowing only in a single direction. In this embodiment, the generator or the like will have a sensing mechanism, such as sensing circuit, which is designed to detect the current flowing in the single direction and equate this to the activation of one of the sections 282, 284.

A first electrical pathway is thus specifically defined by the PCBs 290, the fasteners 300, the conductive member 230, the fingers 171 and one or more wires electrically connecting the fingers 171 to the cable 22. In other words, the connection between the fingers 171 and the conductive member 230 serves to electrically bridge the body 150 and the switch mechanism 110 together. Electrical current flows through the cable 22 and then through the one or more wires to the first finger element 170. The current then flows into the switch mechanism 110 by means of the electrical connection between the fingers 171 and the conductive member 230 once the switch mechanism 110 is actuated by manipulation of one of the switch button members 270.

In a similar manner, the fingers 311 of the second conductive finger element 300 contact and are biased against the body 150 of the handpiece 100. Because the body 150 in this embodiment is formed of a conductive member and is electrically connected to one or more wires of the cable 22, the body 150 comprises a conductive member which can be used to complete the circuit of the switch mechanism 110. The fingers 311 are spaced sufficiently away from the conductive member 230 so that the fingers 171 are actually disposed between the fingers 311 and the conductive member 230 when the switch end cap 200 is attached to the body 150.

The resilient nature of the second sections 314 of the fingers 311 permits the fingers 311 to contact the body 150 and flex inwardly or outwardly relative thereto as the switch end cap 200 is attached. Because the first sections 312 of the fingers 311 are electrically connected to the PCBs 290, the contact between the second ends 314 and the body 150 completes the circuit of the switch mechanism 110 and permits current to flow through the body 150 and the second conductive finger element 310 once the switch mechanism 110 is actuated. In other words, a second electrical pathway is formed and is defined by the PCBs 290, the second conductive finger element 310 and the body 150.

The switch mechanism 110 may be thought of as including four (4) switches with each having a diode in series. More specifically, first raised section 282 of one switch button member 270 corresponds to a first front switch, the second raised section 284 of the one switch button member 270 corresponding to a first rear switch, the first raised section 282 of the other switch button member 270 corresponding to a second front switch, and the second raised section 284 of the other switch button member 270 corresponding to a second rear switch. It will be understood that each of the aforementioned front and rear switches has a diode in series with one another. Preferably, the first and second front switches have the same diode orientation and the first and second rear switches have the same opposite diode orientation. The polarity of the diode depends upon whether the diode is part of the front or rear switches. When a user depresses one of the first raised sections 282, the corresponding first or second front switch will be actuated due to the associated PCB dome collapsing due to the force applied by one of the first posts 276. This causes current to flow in a first direction through the handpiece 100. When a user depresses one of the second raised sections 284, the corresponding first or second rear switch will be actuated due to the associated PCB dome collapsing due to the force applied by one of the second posts 278. This causes current to flow in an opposite second direction through the handpiece 100. Thus, in this embodiment, there are four domes formed as part of the PCBs 290 with two domes being formed on each PCB 290.

The handpiece 100 may be designed so that the front switches comprise maximum power switches with the front diodes thereof serving to signal the delivery of maximum power to the handpiece 100 for maximum vibration of the instrument 30. In this embodiment, the rear switches comprise minimum power switches with the rear diodes thereof serving to signal the delivery of the minimum power to the handpiece 100 for minimum vibration of the instrument 30. The generator is designed so that upon sensing current in the first direction from the actuation of one of the front switches, the generator is programmed to deliver maximum power to the handpiece 100 and similarly, when the generator senses current in the second direction, the generator delivers minimum power to the handpiece 100. If one of the front switches and one of the rear switches are accidently depressed at the same time, the generator will sequentially sense current in both the first and second directions. Upon sensing the opposing currents, the generator is programmed to stop delivering power to the handpiece 100 until the condition is rectified. Preferably, an error or warning message will also appear on the liquid crystal display device 20.

Importantly, the fingers 171 of the first conductive finger element 170 and the fingers 311 of the second conductive finger element 310 do not contact one another during operation of the handpiece 100. If one of the fingers 171 were to contact one of the fingers 311, an electrical short would likely result because the electrical pathways have been crossed. If an electrical short exists in the handpiece 100, the generator will sense current in both the first and second directions, thereby causing the generator to stop delivering power to the handpiece 100 and optionally generate some type of error or warning message.

In another aspect of the present invention, the switch end cap 200 is free to rotate about the handpiece body 150 without disrupting the electrical connection provided between the cable 22 and the switch mechanism 110 housed in the outer shell 201. The one or more ridges 168 formed on the flange member 160 provide annular surfaces for the inner surface 203 of the switch end cap 200 to ride along as the switch end cap 200 is freely rotated about the distal end 154 of the body 150. Because the switch end cap 200 and the body 150 advantageously are electrically connected by the rotatable first and second conductive fingers elements 170, 310, the switch end cap 200 and the body 150 are free to rotate relative to one another without causing an interruption in the flow of current within the handpiece 100. The second sections 174, 314 of the fingers 171, 311, respectively, are sufficiently biased against the corresponding complementary conductive surfaces so that the second sections 174, 314 rotationally slide along these conductive surfaces. Thus, the switch end cap 200 may be rotated about the body 150 to a desired position and continues to remain in electrical communication with the body 150 and the generator regardless of the position of the switch end cap 200. Because most blades 30 are non-symmetrical in nature, the surgeon may prefer to alter the relative position of the switch button members 270 to the instrument 30 which is held in one position within the handpiece 100. The finger elements 170, 310 permit this.

The present embodiments overcome the deficiencies of the conventional surgical devices by a means for providing electrical communication between the switch and other electrical handpiece components without the need for hard wiring. This permits the switch end cap 200 to be easily detached from the body 150 for cleaning and other purposes. For example, the design permits easy inspection of the members providing the electrical communication between the switch end cap 200 and the body 150. Therefore, the integrity of the first and second conductive finger elements 170, 310 may be checked at any time to ensure that they remain in working condition. Also, if the need arises to replace or service either the switch end cap 200 or the handpiece body 150, the two components are quickly and easily separable and replacement or servicing may be done. This permits the surgical operations to continue in an unimpeded manner.

The switch end cap 200 is also ergonomically designed in that the two switch button members 270 are disposed about 180° apart from one another because this provides a preferred orientation where the user (surgeon) may easily contact both switch button members 270 as the handpiece 100 is being grasped by the user. By placing the switch button members 270 in more than one location, the user may easily and quickly manipulate one switch button member 270 closest to the activating finger(s). In other words, it has been found that during a typical manual manipulation of the switch end cap 200, one thumb and one or more fingers are generally positioned 180° apart from another and this complements the positioning of the two switch button members 270. The 180° orientation also has strategic benefits in that if the switch button members 270 were placed at multiple locations, such as three, it would be difficult for the user to grasp the surgical device 10 without possibly contacting and engaging one of the switch button members 270. In the present design, the 180° orientation provides a grasping area in which the user's fingers do not contact the switch button members 270 when the user is holding the device 10. Other design features, e.g., opposing contoured finger sections 212, are designed to also provide the switch end cap 200 with a better feel and permit the user to easily grasp and rotate the switch end cap 200.

The present invention thus provides a surgical handpiece 100 in which the switch mechanism 110 of the switch end cap 200 is electrically connected to the handpiece body 150 in such a manner that permits the switch end cap 200 to be freely rotated about the handpiece body 150 while the electrical connection is maintained.

While the present invention has been described as being a freely rotatable system, it also within the scope of the present invention that the handpiece 100 may be only partially rotatable or non-rotatable. In this instance, a number of stoppers or detents (not shown) are incorporated into the structure of the handpiece 100 so that the switch end cap 200 may only be partially rotated with respect to the handpiece body 150. The degree of rotation may thus be selected by the manufacture and the stoppers or detents positioned accordingly. In another embodiment, the detents may be formed so that the switch end cap 200 is rotated incrementally in a ratchet like manner. Once again, these detents may be formed and complementary engeable features are also formed to provide this ratcheting effect. Also, the handpiece 100 may be designed to provide indexable rotation where the rotation of the switch end cap 200 is indexed relative to the instrument 30. For example, the instrument 30 may be designed so that upon being fastened to the horn 130, the instrument 30 always assumes one orientation. For example, the instrument 30 may assume a north-south (vertical) orientation. By using detents and the like, the rotation of the switch end cap 200 may be indexed so that the switch end cap 200 is initially in a predetermined first position and rotation of the switch end cap 200 causes the switch end cap 200 to rotate in predetermined increments, e.g., 90° increments. This permits the most favored positions of the switch end cap 200 to be provided for by the indexed rotation system.

It will also be understood that the present application broadly discloses a method of providing rotation between the switch end cap 200 and the handpiece body 150 where a predetermined number of conductive pathways are formed by mating electrical conductors. Each pair of mating electrical conductors is designed to convey an independent electrical signal.

Referring to FIGS. 1–8, in another aspect, the present device provides debris resistant coupling between the handpiece body 150 and the switch end cap 200. In each of the embodiments set forth previously with reference to FIGS. 1–8, electrical conduction is made between two conductive members which engage one another in such a manner that rotation between the two conductive members is permitted. In order to provide uninterrupted conduction across the two members, it desirable for the two conductive members to be reasonably free of oxides and residues, such as hard water deposits. It is also preferred to eliminate the need for very clean contacts as this would require timely cleaning and care.

One method of providing effective electrical conduction between the two conductive members is to use sharp, needle-like or pin-like contacts (e.g., finger portions 174, 314) that are optionally spring loaded. The sharp point at the end of the contact increases the pounds per square inch (PSI) contact force and allows penetration of oxides and debris. The contacts may also have a grit-like surface by either disposing a conductive grit material on the surface of the contacts or by modifying the surface of the contacts so that the contacts have a roughened or grit-like appearance. By roughening the surface of the contacts or disposing a gritty material thereon, the contacts are better adept to scrape through any oxide residue or other debris. Rotation of the switch assembly wipes the contact, thereby further improving contact integrity. Another method is to apply a momentary (or on-going) relatively high voltage (DC or AC) to the conductive fingers 171, 311 to break through any oxide barrier. This is especially useful with pointed fingers since the field is higher when applied to a more limited space. Yet another method is to use AC of adequately high frequency, rather than DC, to assess switch status. Any oxide/residue present presents itself as an insulator, creating a capacitor, which the AC couples across.

Figure 8:
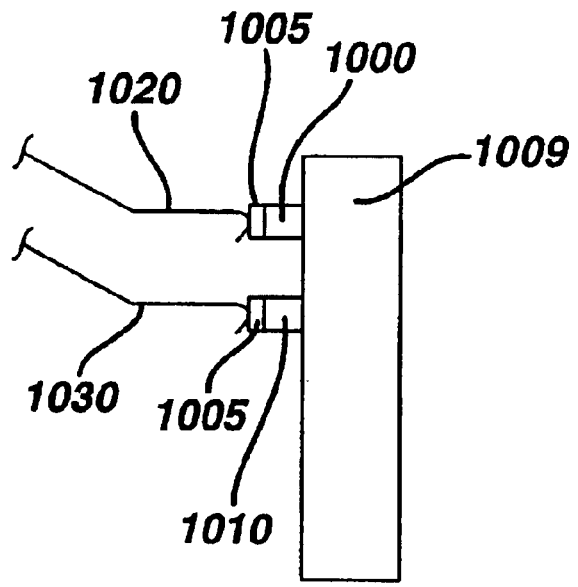
FIG. 8 is a cross section view of one exemplary method of electrically connecting conductive members using a capacitive coupling arrangement between the opposing conductive members.

Referring now to FIG. 8 in which another method is illustrated. In this embodiment, an insulator, in the form of a thin coating and generally indicated at 1005, is applied to the conductive members 1000, 1010 to create a capacitive coupling of the opposing members 1020, 1030. In one exemplary embodiment, the coating 1005 has a thickness from about 0.0001 inch to about 0.002 inch. It will be understood that the conductive members 1000, 1010, 1020, 1030 may comprise any number of types of conductive contact structures, including those set forth previously herein with reference to FIGS. 1–7. For example, the conductive members 1000, 1010, 1020, 1030 may comprise conductive rings, fingers, pins, etc. The conductive member 1000 conductively mates with the conductive member 1020 and conductive member 1010 mates with the conductive member 1030. In the exemplary embodiment, the conductive members 1020, 1030 each comprises a conductive finger assembly, similar to those previously described hereinbefore. AC signals are used to communicate with the switches, at frequencies high enough to consider the potentially insulative coated conductive members 1000, 1010 as a capacitive coupling to the switches. Exemplary frequencies are from about 1 KHz to about 200 KHz. In other words, the conductive member 1010, the coating 1005, and the conductive member 1000 creates a capacitor which thereby permits an AC signal to couple across it. It will be understood that the use of AC signals may be practiced even without the presence of coating 1005 so that if mineralization/debris/oxide contamination occurs, the AC signal is able to couple regardless since intimate metallic contact is not needed.

Referring to FIGS. 1 and 2, in yet another aspect, the handpiece 10 includes mechanism to detect when the switch end cap 200 is attached to the body 150 and also provide a mechanism which discerns which type of switch end cap 200 is attached to the body 150. The communication of switch status across mating conductive members has been previously described in reference to prior embodiments. For example, FIG. 2 shows the first conductive finger element 170 mating with the conductive member 230 and the second conductive finger element 310 mating with the body 150. While this is one particular embodiment, it will be understood that the present invention broadly teaches communicating switch signals across mating conductive members which are rotatable relative to one another.

A circuit (e.g., PCBs 290 in FIG. 6) inside the switch end cap 200 is connected to the electrically conductive members 230, 310 disposed in the switch end cap 200. This circuit presents an impedance or conduction characteristic that can be measured at the conductive members. For example, an AC signal (e.g., 2 KHz) is externally generated and applied to the conductive members 230, 310 of the switch end cap 200 to assess conduction characteristics in both directions of current flow. This permits non-linear and/or polarity dependent conduction and impedance characteristics to be measured. While dual polarity signals provide some additional benefits as will be described below, unipolarity energy can also be implemented.

Figure 9:
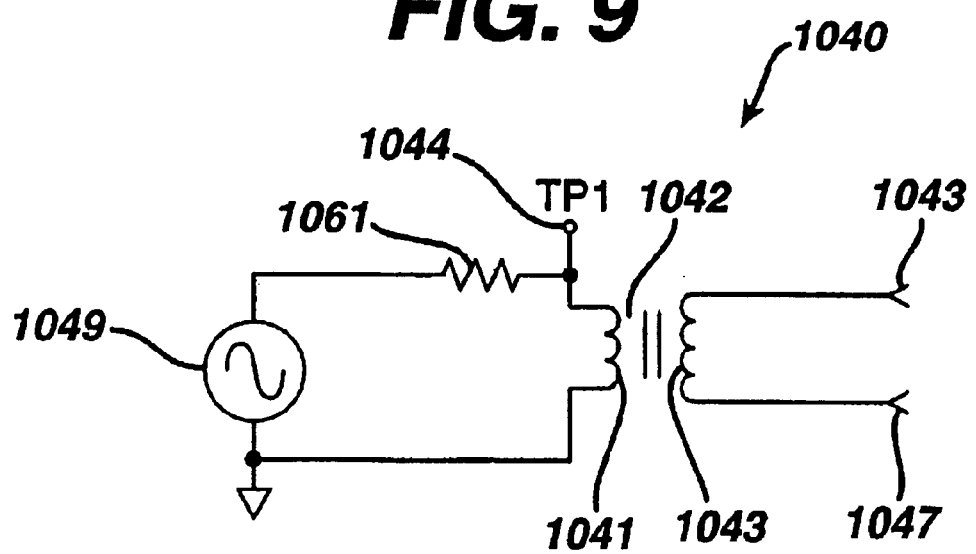
FIG. 9 is a circuit diagram of one exemplary sensing circuit for use in the handpiece assembly.

One example of a sensing circuit 1040 is shown in FIG. 9. The sensing circuit 1040 is formed of a transformer 1042 that has signals applied from a source 1049 to a primary winding 1041 of the transformer 1042. The signals have a predetermined pattern and shape and in one exemplary embodiment, the signals are square or triangle wave pulses. A secondary winding 1043 of the transformer 1042 is connected to the conductive members 1045, 1047 of the body 150 which electrically communicate with the corresponding conductive members (not shown) of the switch end cap 200. It will be understood that the conductive members 1045, 1047 may comprise any number of types of conductive contact structures, including those set forth previously herein with reference to FIGS. 1–7. The transformer 1042 provides signal isolation for patient safety. The pulse magnitude seen at TP1 1044 is proportional to the conductivity across the conductive members. The pulses are bi-polar, with the positive pulse amplitude proportional to conductivity in one direction and the negative pulse amplitude proportional to conductivity in the opposite direction.

Figure 10:
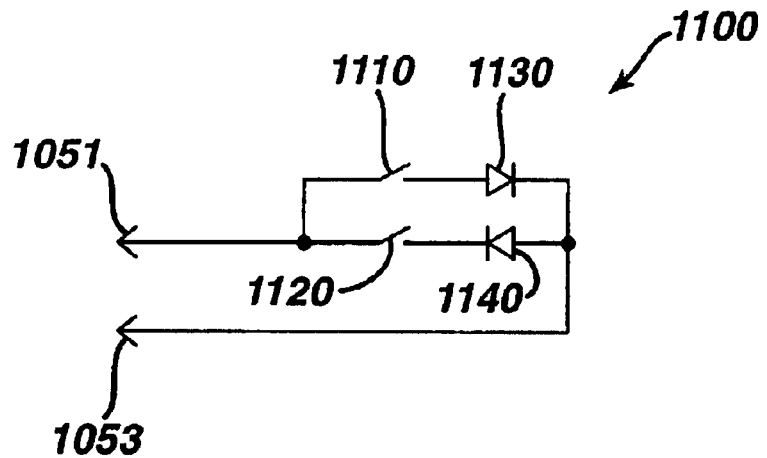
FIGS. 10 and 10(a) thru 21 are circuit diagrams showing various embodiments of circuits for use in the switch end cap according to one embodiment.

The signal at TP1 1044 portrays the amount of conduction in each direction across the conductive members 1045, 1047. The output has pulses that are both positive and negative. The amplitude of the positive pulses portrays the amount of conduction in one direction and the amplitude of the negative pulses portrays the amount of conduction in the other direction. The generator in the console 20 (FIG. 1) monitors the TP1 1044 and is thereby able to determine the conduction status in each direction of current flow across the conductive members 1045, 1047. An example of a circuit 1100 for use in the switch end cap 200 is shown in FIG. 10. Each of the two switches, generally indicated at 1110, 1120, which form a part of the switch mechanism 110 (FIG. 5) is connected to its own diode 1130, 1140, respectively. One of the switches 1110, 1120 is connected to a cathode of its diode 1130, 1140, respectively, and the other of the switched 1110, 1120 is connected to an anode of its diode 1130, 1140. For purpose of illustration only, the switch 1110 will be discussed as being connected to the anode of its diode 1130 and the switch 1120 will be discussed as being connected to the cathode of its diode 1140. Each of the switches 1110, 1120 has the diode attached opposite of the other switch 1110, 1120. This method permits the use of two conductors to communicate the status of two switches 1110, 1120 across rotatable sets of contacts (e.g., the rotatable contacts shown in FIGS. 1–7). Traditionally and without the use of the circuit of FIGS. 9–10A, three contact pairs would be required to communicate the status of two switches 1110, 1120. By reducing the number of sets of contacts which are required to communicate the status of the switches, the switch mechanism advantageously occupies less space within the interior of the handpiece resulting in a more compact design.

An AC signal is applied to the conductive members 1051, 1053 of the switch end cap 200. Conduction detected in only one direction using a sensing mechanism, such as the sensing circuit 1040 of FIG. 9, indicates that one of the switches 1110, 1120 is depressed, while conduction only in the opposite direction indicates that the other of switches 1110, 1120 is depressed.

In the example, shown in FIG. 9, a square wave generator provides about a 2 KHz 9 Volt peak-to-peak signal the primary winding 1041 and includes a resistor 1061 in series with the primary winding 1041 as a means for measuring the current through the transformer 1042 and a voltage a across the transformer 1042. The voltage is monitored at TP1 1044.

When the conductive members 1045, 1047 have no conduction capability across them (i.e. none of the switches in the switch end cap are closed and no debris is present across the members 1045, 1047), then the TP1 signal has a relatively large peak positive voltage of about +9 volts and a relatively large peak negative voltage of about −9 volts. The peak voltage is reduced according to the degree of conduction sensed, with the polarity of conduction influencing the particular associated polarity peak, without substantially influencing the opposite polarity peak.

The open/closed status of switch 1110 is portrayed via the magnitude of one polarity peak voltage. The magnitude is relatively high, e.g., about 9 volts, when the switch 1110 is open. The magnitude is relatively low, e.g., about 3 volts, when the switch 1110 is closed. The same aspects apply for switch 1120 except that the magnitude of the opposite polarity is influenced instead. The circuit 1100 provides a means for monitoring the status of two independent switches 1110, 1120 with just two conductive members 1051, 1053 rather than the three or more conductive members that would be required in a more traditional form of circuit monitoring. This reduction in conductive members also allows the handpiece to be made more reliable.

Debris across the conductive members 1045, 1047 will be conductive in both directions, which is readily detectable by the circuit 1040 and is used to determine if debris is present. If conduction is seen in both directions, both the positive and negative peaks will drop to intermediate or low magnitudes. The generator (in console 20—FIG. 1), monitoring the TP1 1044, will detect that there is conduction in both directions and recognize that simultaneous conduction in both directions as an invalid input. This results in disabling the activation of handpiece and/or alert the user to a problematic condition. Thus, the circuit provides a means for being resistant to inadvertent activation due to debris being across the conductive members 1045, 1047, such as saline or blood.

The circuit 1040 also provides yet another function of detecting the presence of fluid inside the handpiece since the fluid will bridge the switch circuitry inside the handpiece and typically result in dual polarity conduction across the traces. The effect is similar to conductive fluid across the conductive members 1045, 1047, which can be detected by the generator and disable activation or alert the user. It may be useful to use circuit 1040 to detect the presence of fluid inside a handpiece independently of switch circuitry.

Figure 10A:
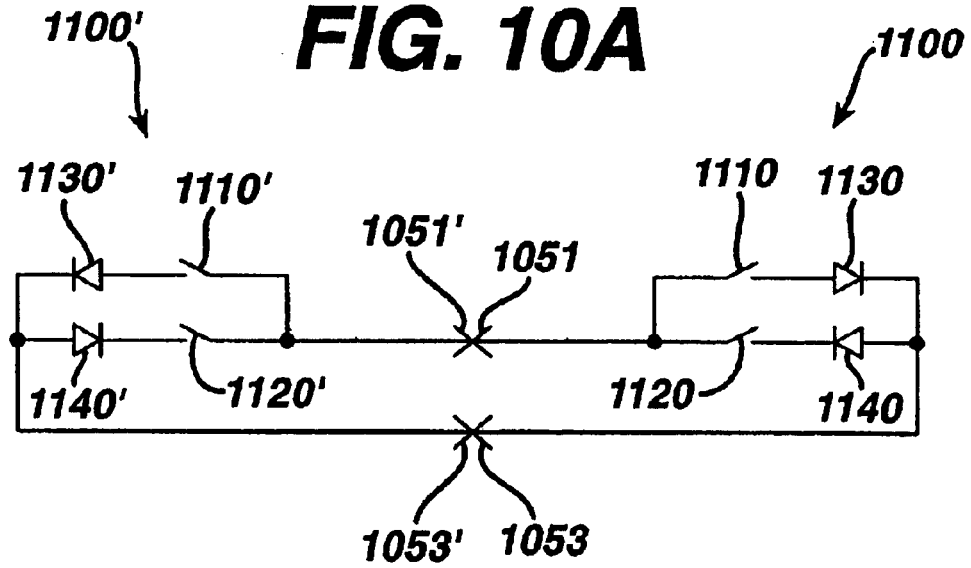

The circuit of FIG. 10 serves one pair of switches 1110, 1120, such as a rocker on one side of the handpiece. An identical circuit 1100' can serve another pair of switches 1110', 1120' located on another position on the handpiece, such as a rocker located 180° away. Such a circuit 1100' is shown in FIG. 10A. FIG. 10A illustrates two circuits 1100 which are connected in parallel to one another so that the status of four buttons may be communicated along two lines using the circuit design of FIG. 10A. More specifically, the two conductive members 1051, 1051' are electrically connected in parallel as well as two conductive members 1053', 1053' being likewise electrically connected in parallel. In this manner the status of any one of the switches 1110, 1110', 1120, 1120' may be monitored using the same sensing circuit 1040 shown in FIG. 9 or any other suitable sensing design.

Another additional benefit of the circuit 1040 is the ability to disregard inadvertent activation of opposing function switches such as the maximum on one side and minimum on one side. Since pressing the sections of the switch associated with the maximum and minimum functions results in bi-directional conduction, the generator in the console 20 (FIG. 1) considers this input as invalid. This enhances safety of the operation.

Figure 11:
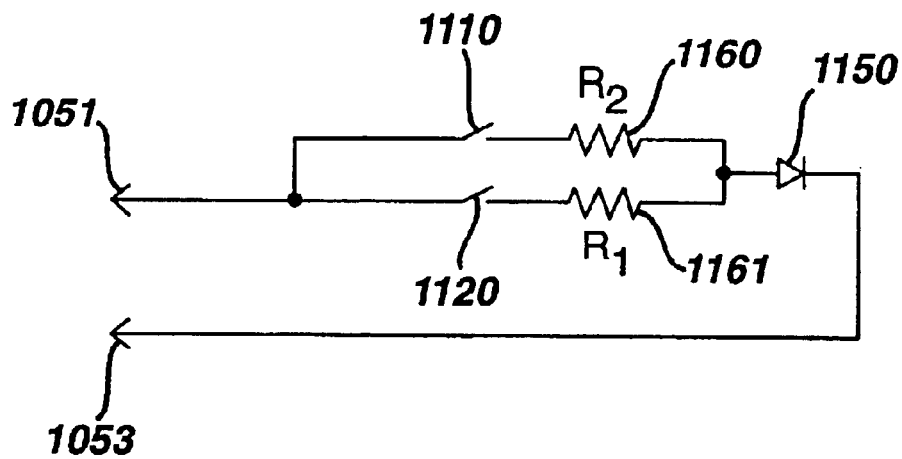

Another benefit of the configuration of FIG. 10 is the ability of the circuit 1100 to detect resistive shorting caused by debris/fluid across the conductive members 1051, 1053 since the conduction is bi-directional and can be discerned by the sensing circuit 1040 (FIG. 9). The amount of conductive debris artifact can be measured when neither switch 1110, 1120 or just one of the switches 1110, 1120 is depressed. A variation of the circuit 1100 is to use one diode 1150 that is shared by both switches 1110, 1120 and connect each switch 1110, 1120 via resistors 1160, 1161 as shown in FIG. 11. The sensing circuit 1040 will see conduction only in one direction when one of switches 1110, 1120 is depressed and the degree of conduction is determined by the resistance value. In one exemplary embodiment, resistor 1161 has a value of 0 Ω and resistor 1160 has a value of about 100–1000 Ω. This method has the benefit in that there is no conduction in the opposite direction, except if there is debris. Thus, the amount of artifact contributed by debris can be detected at all times, even when both switches are depressed. The debris resistance value can be used to recalculate the actual resistance connected via a closed switch, thereby improving ability to discern which of the switches 1110, 1120 is depressed in spite of debris.

Figure 12:
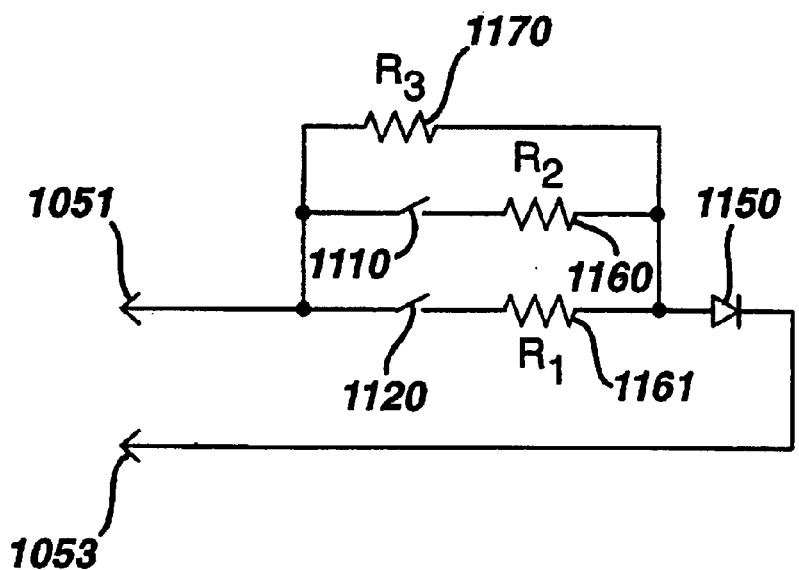

In another embodiment shown in FIG. 12, a resistor 1170 is added across the switches 1110, 1120. By adding this resistor 1170, the conductive member series contact resistance can be determined since the single-direction conduction, especially when the switches 1110, 1120 are open, can be measured and compared to the expected resistance in that direction. In one exemplary embodiment, resistor 1170 has a value of 2 KΩ, resistor 1061 has a value of 0 Ω and resistor 1060 has a value of about 100–1000 Ω. Combining this data with data related to conduction in the opposite direction (debris) allows accurate assessment of contact condition.

Figure 13:
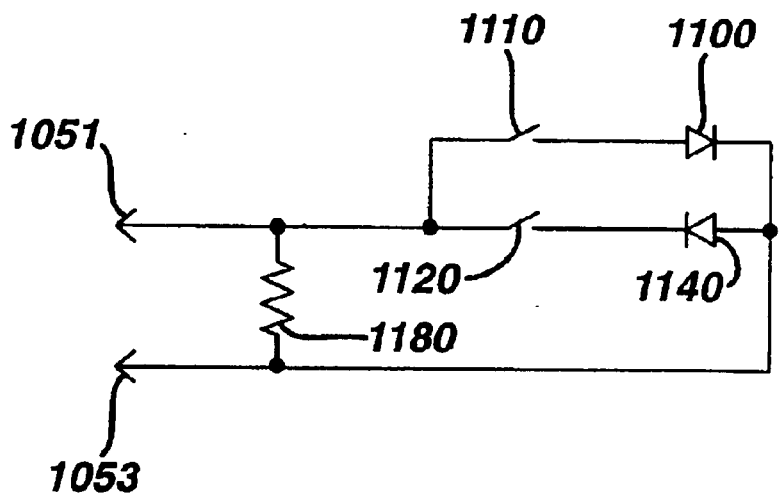

According to one embodiment, the same two conductive members 1051, 1053 of the switch end cap 200 can be used to detect the presence and type of switch end cap 200 attached to the handpiece body 150. One method, shown in FIG. 13, is to connect a resistor 1180 across the conductive members 1051, 1053 of the switch end cap 200 for a switch end cap 200 that contains one or more switches. The resistor 1180 may have a value from about 500 Ω to about 5000 Ω. The presence of this resistor 1180 can be measured to detect the presence of a switch-style end cap 200. If the non-switch-style end cap 200 has no resistor (or a different value resistor), then the resistance of the conductive members 1051, 1053 is extremely high, e.g., about 1 M Ω (or a different resistance value), thereby indicating that a non-switch-style end cap 200 is attached.

Figure 14:
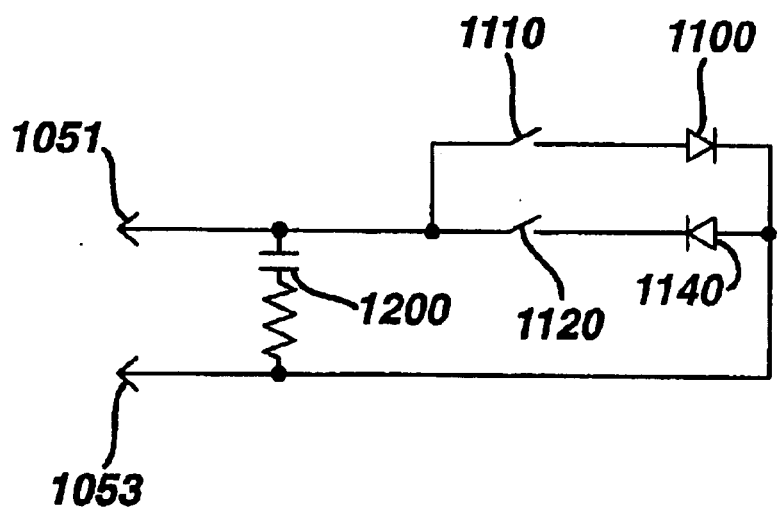

Thus, a specific resistance value can be used according to the type of switch end cap 200 to further distinguish between various types of end caps and thereby provide an identification. One limitation of this type of resistance method is that the linear resistance of debris on the conductive members 1051, 1053 can influence the measured result. This could lead to erroneous identification, or at the least, produce a resistance that is not expected. One method for addressing the debris-induced error in resistor measurement of the switch end cap 200 identification is shown in FIG. 14. In this embodiment, a capacitor 1200 is placed across the conductive members of the switch end cap 200. An appropriately chosen capacitor 1200 has a high impedance at nominal frequency used during switch query (e.g., 2 KHz), but becomes a low impedance when a higher frequency is applied, proportional to the frequency. Thus, various capacitor values (or capacitor in series with a resistor) may be chosen to identify a particular type of switch end cap 200. The debris impedance is resistive and the capacitor impedance is frequency dependent. Thus, the sensing circuit 1040 (FIG. 9) is able to measure the debris resistance at lower frequency and then measure the combined impedance at a higher frequency. Thus, provision is made to make an identification in spite of debris.

Figure 15:
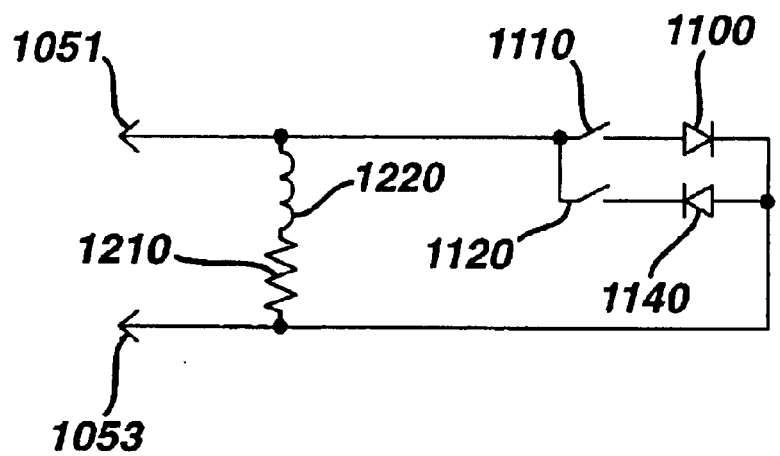

A similar approach is shown in FIG. 15. In this embodiment, a resistor 1210 is used in series with an inductor 1220 (or using an inductor with a high internal resistance, which serves as the resistor). At the lower frequency, the inductor 1220 is a lower impedance, thus the resistor value is placed across the conductive members 1051, 1053. At a higher frequency, the resistor conduction is relatively blocked and the debris across the conductive members 1051, 1053 can be measured. Thus, the debris resistance can be taken into account and the debris is not easily able to disrupt the resistor identification method.

Figure 16:
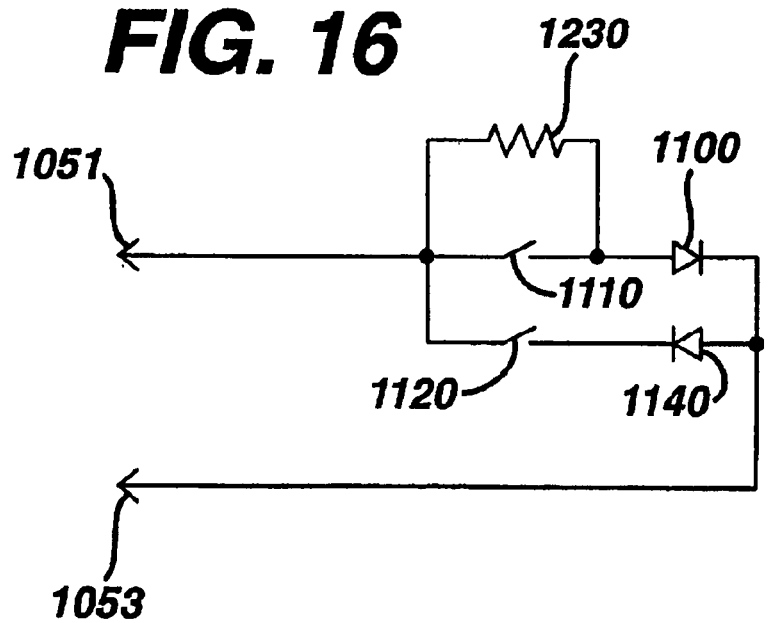
Figure 17:
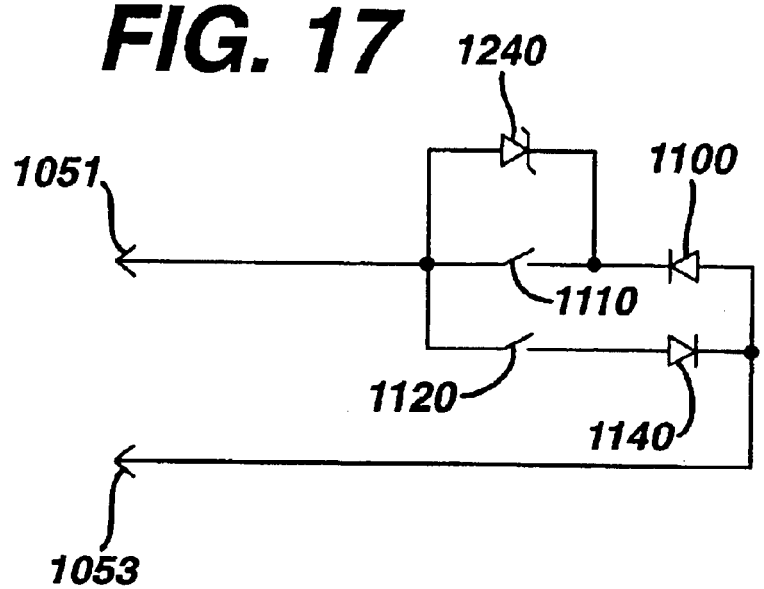
Figure 18:
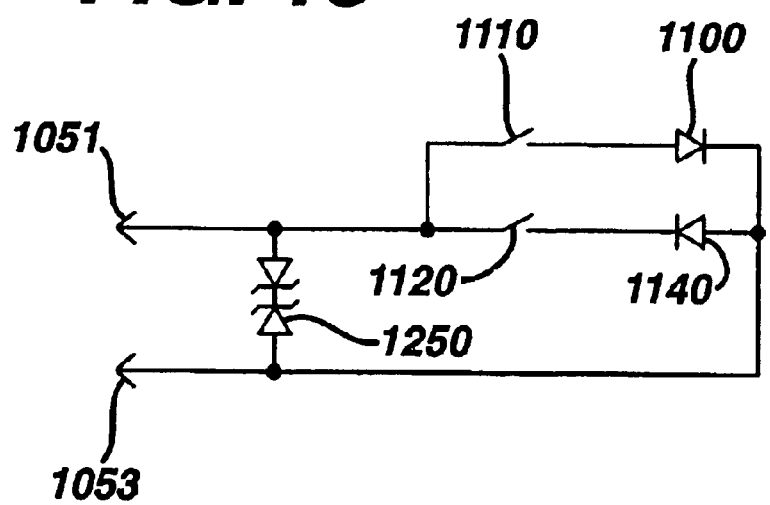
Figure 19:
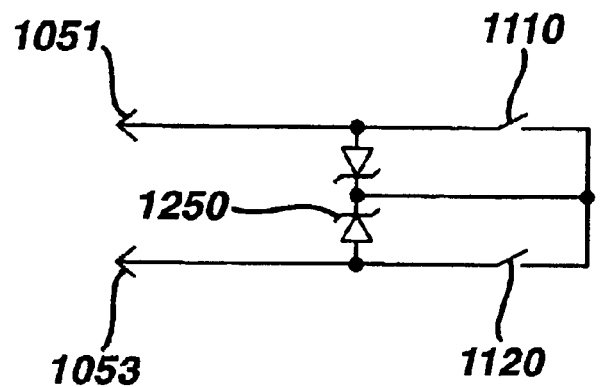
Figure 20:
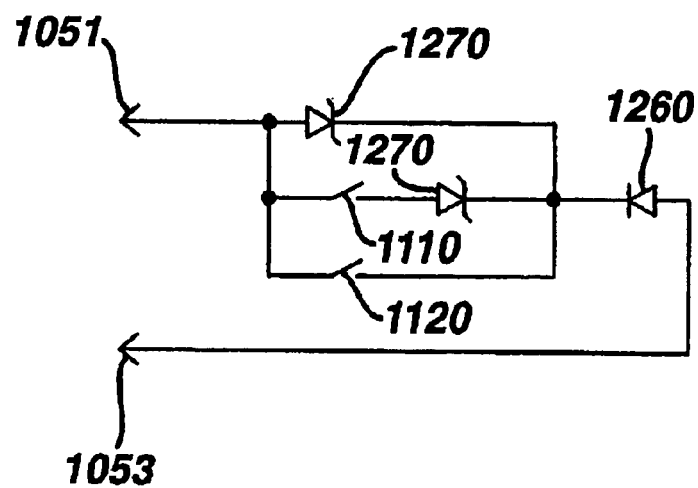
Figure 21:
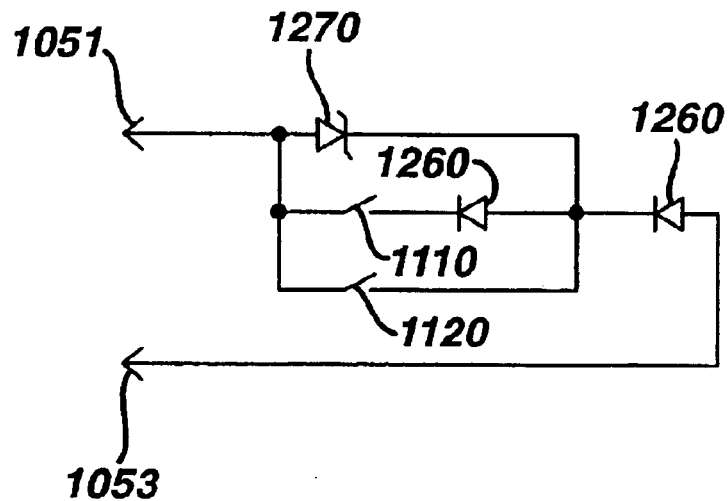

As shown in FIG. 16, to address the concern of debris resistance artifact, a resistor 1230 is in series with the diode 1100 such that the resistance only conducts in one direction. This allows the sensing means to determine the resistance of the debris in one direction of current and the combined resistance of debris and identification resistor in the alternative direction of the current. As shown in FIG. 17, instead of using a diode in series with a resistor, the resistor 1230 can be replaced with a zener diode 1240 that is several volts lower than the peak applied voltage. The zener diode 1240 is out of circuit in one direction and conducts in the opposite direction at avalanche voltage, which can be detected. Another method, as shown in FIG. 18, is to use a back-to-back zener diode or transorb device 1250 that is connected across the conductors 1051, 1053. This device 1250 will conduct current in both directions when the voltage reaches avalanche. This method is useful when space constraints are tight and one component needs to perform multiple functions, such as electrostatic discharge protection and identification of the switch end cap 200. A further variation, as shown in FIG. 19, is to use the back-to-back zener diode 1250 also as the diodes used by the switches 1110, 1120. This further reduces the component count. In this embodiment, the zener device 1250 provide identification of the switch end cap 200, switch conduction control, and electrostatic discharge protection. FIGS. 20 and 21 show other alternative circuit structures for using a diode 1260 or zener diode 1270 to create switch conduction level and identification.

In other embodiments, detection of fluid/debris that may otherwise not be detectable is made possible. The use of the above-described circuitry permits the detection of fluid/debris bridging switch contacts or other regions of a circuit board, slip rings, etc. This is made possible by monitoring the level of signals. Detection of fluid/debris can be used to alert the user to the condition and/or to lock out use of the handpiece 100. Some reasons for such detection, alert and/or lock-out include but are not limited to avoid use of a contaminated handpiece 100, prevent operation of the handpiece 100 in a compromised electrical/mechanical condition, block use when the handpiece 100 has been excessively used and is now in a worn state.

In many switch devices, including those disclosed herein, negative and positive peaks of the switch signal indicate the open/closed status of each switch. In the event that fluid/debris were to ingress into the handpiece 100 and reside on the switch, the conduction is resistive. For example, during a cleaning (e.g., autoclave) operation, moisture may ingress in and ultimately precipitate as distilled water within the handpiece 100. This resistive conduction results in a signal that is in between a switch open signal and a switch closed signal. Signals in the "in between" range can be detected and used to indicate to the user a fluid/debris ingress condition or the signals can be used to block handpiece use.

While the circuitry described hereinbefore is suitable for use, other conduction detection circuits may be used according to this embodiment. The focus of this embodiment is to detect unexpected resistive conduction across circuits and switches, which indicates high likelihood of fluid/debris ingress into undesired areas. Placement of exposed conductors in predetermined, select areas, such as on a printed circuit board or elsewhere inside the handpiece 100, can act as a sensing means for detection of fluids elsewhere in the handpiece, not just at the switch locations of the handpiece 100.

Figure 22:
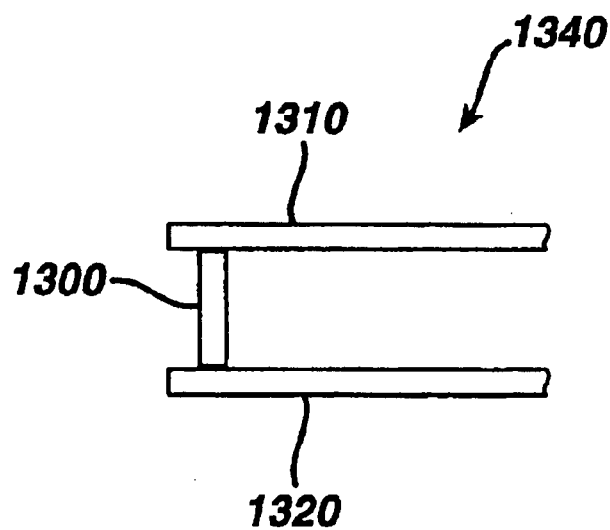
FIG. 22 is a cross section view of a sensor used to detect fluid/debris within the handpiece.

As generally shown in FIG. 22, the detection of fluid/debris ingress can be further enhanced by the placement of a reactive material 1300 in close proximity to two conductive members 1310, 1320. In this embodiment, the components 1300, 1310, 1320 form a sensor 1340 for detecting fluid/debris ingress. The reactive material 1300 has a low conductivity when dry but facilitates conduction when wet or due to exposure to another chemical reaction. For example, salt crystals 1300 or the like can be placed between two opposing, spaced sensing wires 1310, 1320. In itself, salt crystals 1300 are not conductive; however, they are reactive such that moisture causes the crystals 1300 to become conductive. The reactive material 1300 can be placed on surfaces of the conductive members 1310, 1320 or a bridge (not shown) that may extend therebetween. In addition, the reactive material 1300 can be disposed so as to form a bridge between the conductive members 1310, 1320. This conduction-when-wet facilitation is useful for detection of fluids having a relatively low conductivity, such as steam condensate. Thus, in this embodiment, the sensor 1340 detects fluid/steam ingress. In the illustrated embodiment, the sensor 1340 is formed of exposed conductive members 1310, 1320 (e.g., wires or switch contacts) that are monitored by an electronic circuit such as those described hereinbefore. Thus, the sensor 1340 is incorporated into the switch contact circuitry.

Besides detecting fluid induced conduction between the switch contacts, other sensors and wire gaps can also be used to detect fluid ingress elsewhere within the handpiece 100. In other words, the sensor 1340 may be separate from the switch circuitry and provided in a different location within the handpiece 100. In this instance, the sensor 1340 can simply be connected to the same contacts as the switches, thereby using the same sensing circuit as that used by the switches. Alternatively, the sensor 1340 may be simply connected to a controller (e.g., the same controller which is connected to the sensing circuitry) such that controller detects a signal generated by the sensor 1340 include the presence of fluid/debris by the sensor 1340.

The identity of each type of switch assembly attached to the handpiece body 150 (i.e., a different model or style or function) can be determined by using variations of the circuits previously described with each variation representing one particular type of switch assembly. For example, a resistor could be placed across the variable switch for a "type 1" switch assembly and for "type 2" switch assembly, the resistor is instead placed across the "full" switch. Thus, for type 1, the negative peak is influenced, while for type 2, the positive peak is influenced. The conduction sensing circuit 1040 (FIG. 9) can determine which peak is being influenced by the resistor and thereby determine the switch assembly type. Various resistor values across a switch can also be used for identification purposes, which results, in different peak voltages with each peak voltage value representing a particular kind of switch assembly.

When a capacitor is used across the conductive members 1051, 1053 in the switch assembly, the value for each capacitor is varied so that each switch assembly type has a different capacitor value. By sweeping/changing, the frequency used by the sensing circuit 1040 (FIG. 9), the sensing circuit 1040 can determine the capacitor value and conclude the type of switch assembly attached. Other methods include placing a zener diode across the variable switch for type 1 identification and placing the zener diode across the full switch for type 2 identification. It will be further appreciated that the embodiments described herein may be applied to other types of devices where switches control functions besides variable and full ultrasonic medical device controls.

Incorporating switch button members 270 onto handpiece 100 provides a convenient method of operating the handpiece 100. However, there are situations where these switch button members 270 should preferably be disabled. For example, when the handpiece 100 is grasped tightly over the button members 270 and instead is activated by a foot pedal. Another example is when the handpiece 100 is laid down during non-use on a contorted surface that may act to depress the button members 270. The button members 270 can also be disabled via the "standby" mode of the generator.

Another method to disable button members 270 is by means of a disable switch (not shown) located remote from the handpiece 100, such as a switch on the front panel of the generator console. Furthermore, the generator can be placed into standby mode to disable the finger switches and the foot pedal. Disabling button members 270 via the console front panel can be awkward due to the fact that the handpiece 100 is sterile and the console is not, making the disable function on the front panel impractical to touch by the handpiece user. Thus, a disabling operation in this type of configuration requires the user to be exposed to a non-sterile environment. This is contrary to many procedural guidelines.

Another method to disable button members 270 is to place another switch (not shown) on the handpiece 100 that serves as a disable function. However, an additional switch on the handpiece 100 takes up space, adds expense and complexity.

According to the embodiments disclosed herein, detection circuitry is incorporated into the handpiece system such that the handpiece button members 270 are continuously monitored by one detection circuit. However, the system can be configured so that the ability of the button members 270 to activate the console output can be disabled. In other words, the user can disable the button members 270 under select conditions. One method of accomplishing this is to disable the button members 270 via the existing button members 270 on the handpiece 100. For example, a unique switch operation sequence can be used such that when the user depresses one or more of the button members 270 according to this unique switch operation sequence, the button members 270 become disabled. It will be appreciated that this unique switch operation sequence should not be a sequence expected during operative use of the handpiece 100 as this would result in unintended disablement of the handpiece 100. Similarly, this sequence should also not be a sequence typically seen during random handling of the handpiece.

The system may be configured so that the button members 270 are reactivated by merely depressing one or more of the button members 270 or by pressing one or more of the button members 270 according to a predetermined reactivation pattern.

One exemplary operation sequence utilizes the fact that there are two button members 270, e.g., two rocker switches. Each rocker button member 270 has two raised sections 282, 284 with one activation mode (e.g., full operation) being represented by one of the raised sections 282, 284 and the other of the activation modes (e.g., variable operation) being represented by the other of the raised sections 282, 284. In this embodiment, the rocker button members 270 are formed of a rigid material and each pivots about a point, thereby preventing both ends from being depressed simultaneously. If the user accidently presses down one activation mode on one button member 270 and also simultaneously presses down the other activation mode on the other button member 270, the handpiece 100 becomes disabled. In this instance, the opposite activation modes on opposite switches are depressed simultaneously (i.e., within 0.3 second of each other) and are held down for a predetermined period of time. The opposite activation modes are then released shortly thereafter (i.e., 0.3 to 0.6 second later and within 0.3 second of one another). A monitoring circuit detects this particular sequence (opposite activation modes on opposite switches being held down at the same time and then released generally simultaneously from one another) and causes the button members 270 to be disabled from performing activation or the generator is set into standby mode.

In this exemplary embodiment, the user can re-enable the button members 270 or bring the generator out of standby by using the generator front panel (e.g., depressing a button thereon) or by repeating (or inverting) the rapid alteration of finger switch depressions.

In another sequence example, the sequenced depression of a single switch according to a predetermined sequence pattern results in the disablement or reactivation of the button member 270. For example, the rapid alternation of one mode, the other mode, and then the one mode causes the disablement (reactivation) of the handpiece 100. In other words, if the user presses the full activation mode and then the variable activation mode and finally the full activation mode again on the same button member 270, the monitoring circuit will detect such sequenced actions and cause the disablement (reactivation) of the handpiece 100. It will be understood that the sequence may be reversed (i.e., variable-full-variable) or that another sequence can be programmed so that the monitoring circuit causes disablement (reactivation) upon detecting the sequenced action of the user. Each depression is for only a brief period of time (e.g., 1 second). Again, the user can re-enable the button members 270 or bring the generator out of standby by either manipulating a control on the front panel of the generator or by repeating (or inverting) the rapid alteration of the finger switch depressions.

One will appreciate while the rocker type switches disclosed herein have two discrete raised sections (representing two activation modes), the above-described disablement method applies equally to handpiece configurations which have separate switches on one side and separate switch on the opposite side.

In another embodiment, the button member 270 is an elastomeric rocker that is typically pressed at one end or the other end. For example, the button member 270 is pressed at either the first raised section 282 or the second raised section 284. Unlike the above-described rigid rocker switch, the elastomeric nature of the rocker button member 270 permits both ends of the button member 270 to be depressed simultaneously. In order to evoke a disable/enable operation, both ends (e.g., raised sections 282, 284) of the button member 270 are depressed simultaneously. Thus, simultaneously pressing both ends of one button member 270 evokes a disable condition, whereby the handpiece 100 is disabled. The switch 210 can be re-enabled by a subsequent simultaneous depression of both ends. While the rocker type button member 270 has fairly light touch operation when depressing only one end of the rocker at a time, the rocker can be designed to require more pressure when pressing both ends simultaneously to obtain switch contact closure. Thus, the special function that is elicited by pressing both ends simultaneously requires substantially more pressure than light pressure for normal use. This higher pressure operation has the distinct benefit of being less apt to be initiated inadvertently, thus eliminating the series of switch depressions described in the above examples.

It will further be appreciated that any of the above exemplary disablement techniques can alternatively be used to perform other functions normally otherwise only accessible at the front panel of the console. Other functions that could be performed by the button members 270 include but are not limited to: performing a self test, changing a control setting, or modifying other front panel settings without the handpiece user having to contact the front panel.

It will further be understood that the handpiece 10 set forth in FIG. 1–7 is merely exemplary and the above-described circuitry and detection means may be employed in other handpieces, such as those disclosed in commonly assigned U.S. patent application Ser. No. 09/693,549, entitled "Conductive Finger Adapter Retention to Reduce Number of Conductors", filed Oct. 20, 2000, which is incorporated herein by reference in its entirety and handpiece 10 is preferably used in a surgical system, such as the one disclosed in commonly assigned U.S. patent application Ser. No. 09/693,621, entitled "Ultrasonic Surgical System", filed Oct. 20, 2000, which is incorporated herein by reference in its entirety.

While the invention has been particularly shown and described with reference to the preferred embodiments thereof, it will be understood by those skilled in the art that various changes in form and detail may be made therein without departing from the spirit and scope of the invention.

What is claimed is:

1. A sensing circuit for a switch end cap of a hand piece, comprising:
   a plurality of switches connected in parallel;
   a plurality of diodes respectively connected in series to each of the plurality of switches,
      wherein the plurality diodes are connected to each other in reverse polarities;
   a plurality of conducting members connected to the plurality of diodes and the plurality of switches,
   wherein each of the plurality of conducting members respectively communicate with a plurality of corresponding conductive members of the switch end cap;
   a transorb connected in parallel with the plurality of conducting members,
      wherein the transorb comprises zener diodes connected in a back-to-back configuration; and
   wherein the circuit detects a presence of excessive debris associated with the handpiece.

2. The sensing circuit of claim 1, further comprising:
   a resistor connected in parallel with the plurality of conducting members.

3. The sensing circuit of claim 1, further comprising:
   a resistor; and
   a device connected in series with the resistor.

4. The sensing circuit of claim 3, wherein the resistor and device are connected in parallel with the plurality of conducting members.

5. The sensing circuit of claim 4, wherein the device is one of a capacitor and an inductor.

6. The sensing circuit of claim 1, further comprising:
   a device connected in series with a diode from the plurality of diodes;
   wherein a resistance of debris is determined in a single direction of current.

7. The sensing circuit of claim 6, wherein the device is one of a resistor and zener diode.

8. The sensing circuit of claim 1, further comprising:
   a sensor in close proximity to the plurality of conducting members.

9. The sensing circuit of claim 8, wherein the sensor comprises a reactive material.

10. The sensing circuit of claim 9, wherein the reactive material has a low conductivity when dry and facilitates conduction when one of wet and exposed to a chemical reaction.

11. The sensing circuit of claim 1, wherein two circuits are connected in parallel such that a status of multiple buttons on the handpiece is obtained.

12. The sensing circuit of claim 11, wherein the status of four buttons is obtained.

13. The sensing circuit of claim 12, wherein two sensing circuits are connected in parallel, and two conducting members are connected in parallel.

* * * * *